(12) United States Patent
Kim et al.

(10) Patent No.: US 10,098,613 B2
(45) Date of Patent: Oct. 16, 2018

(54) IMAGE PROCESSING MODULE, ULTRASOUND IMAGING APPARATUS, IMAGE PROCESSING METHOD, AND CONTROL METHOD OF ULTRASOUND IMAGING APPARATUS

(71) Applicants: SAMSUNG ELECTRONICS CO., LTD., Suwon-si (KR); Industry Academic Cooperation Foundation, Hallym University, Chuncheon-si (KR)

(72) Inventors: Kyu Hong Kim, Seongnam-si (KR); Sung Chan Park, Suwon-si (KR); Su Hyun Park, Hwaseong-si (KR); Joo Young Kang, Yongin-si (KR); Jung Ho Kim, Yongin-si (KR); Moo Ho Bae, Seoul (KR)

(73) Assignees: SAMSUNG ELECTRONICS CO., LTD., Suwon-si (KR); Industry Academic Cooperation Foundation, Hallym University, Chuncheon-si (KR)

( * ) Notice: Subject to any disclaimer, the term of this patent is extended or adjusted under 35 U.S.C. 154(b) by 458 days.

(21) Appl. No.: 14/328,233

(22) Filed: Jul. 10, 2014

(65) Prior Publication Data
US 2015/0016215 A1    Jan. 15, 2015

(30) Foreign Application Priority Data
Jul. 11, 2013    (KR) .................... 10-2013-0081651

(51) Int. Cl.
*G03B 42/06*    (2006.01)
*A61B 8/08*    (2006.01)
(Continued)

(52) U.S. Cl.
CPC ........ *A61B 8/5207* (2013.01); *G01S 7/52047* (2013.01); *G01S 7/52085* (2013.01); *A61B 8/4405* (2013.01); *G01S 15/8927* (2013.01)

(58) Field of Classification Search
USPC .......................................................... 367/11
See application file for complete search history.

(56) References Cited

U.S. PATENT DOCUMENTS 6,436,044 B1    8/2002  Wang
6,446,862 B1 *  9/2002  Mann ................. G07C 9/00087
                                                                235/380
(Continued)

FOREIGN PATENT DOCUMENTS

KR    19970031484 A    6/1997
KR    10-0911879 B1    8/2009
(Continued)

OTHER PUBLICATIONS

Pettersson, Michael. "Toeplitz Covariance Matrix Estimation for Adaptive Beamforming and Ultrasound Imaging." (2012).*
(Continued)

*Primary Examiner* — Isam A Alsomiri
*Assistant Examiner* — Jonathan D Armstrong
(74) *Attorney, Agent, or Firm* — Sughrue Mion, PLLC

(57) ABSTRACT

An image processing module includes an input unit, a weight operator, and a synthesizer. The input unit is configured to receive a plurality of input signals of a plurality of channels. The weight operator is configured to calculate at least one weight to be applied to each channel based on at least one converted signal. The at least one converted signal is acquired by converting at least one input signal among the plurality of input signals of each channel, or by converting a synthesized input signal of the plurality of input signals of each channel. The synthesizer is configured to synthesize the
(Continued)

plurality of input signals of the plurality of channels using the weight.

12 Claims, 24 Drawing Sheets

(51) Int. Cl.
*G01S 7/52* (2006.01)
*G01S 15/89* (2006.01)
*A61B 8/00* (2006.01)

(56) References Cited

U.S. PATENT DOCUMENTS

| | | | |
|---|---|---|---|
| 6,482,160 B1 | 11/2002 | Stergiopoulos et al. | |
| 6,490,448 B1* | 12/2002 | Hogberg | H04B 7/18543 342/354 |
| 7,085,393 B1* | 8/2006 | Chen | H04S 1/007 381/1 |
| 9,350,402 B1* | 5/2016 | Corbalis | H04B 1/123 |
| 9,853,668 B2* | 12/2017 | Corbalis | H04B 1/123 |
| 2006/0056641 A1* | 3/2006 | Nadjar | A61B 7/04 381/67 |
| 2009/0234230 A1* | 9/2009 | Bercoff | G01S 7/52049 600/447 |
| 2010/0183158 A1* | 7/2010 | Haykin | H04R 25/552 381/23.1 |
| 2011/0261977 A1* | 10/2011 | Hiroe | G10L 21/0272 381/119 |
| 2012/0196591 A1* | 8/2012 | O'Keeffe | H01Q 3/2605 455/427 |
| 2013/0272548 A1* | 10/2013 | Visser | G06K 9/00624 381/122 |
| 2014/0031689 A1* | 1/2014 | Kang | G01S 15/8977 600/443 |
| 2014/0358557 A1* | 12/2014 | Sen | G10L 19/02 704/500 |
| 2015/0016215 A1* | 1/2015 | Kim | G01S 7/52047 367/7 |
| 2017/0307435 A1* | 10/2017 | Park | G01H 3/125 |

FOREIGN PATENT DOCUMENTS

| | | |
|---|---|---|
| KR | 10-1109326 B1 | 2/2012 |
| KR | 10-1214820 B1 | 12/2012 |
| KR | 10-2013-0054743 A | 5/2013 |

OTHER PUBLICATIONS

Kazanci, Oguz R., and Jeffrey L. Krolik. "Beamspace adaptive channel compensation for sensor arrays with faulty elements." Conference Record of the Thirty-Ninth Asilomar Conference on Signals, Systems & Computers. 2005.*

Communication dated Jun. 19, 2017, issued by the Korean Intellectual Property Office in counterpart Korean Application No. 10-2013-0081651.

Communication dated Dec. 8, 2017, issued by the Korean Intellectual Property Office in counterpart Korean Application No. 10-2013-0081651.

Communication dated Feb. 8, 2018, issued by the Korean Intellectual Property Office in counterpart Korean Application No. 10-2013-0081651.

* cited by examiner

IMAGE PROCESSING MODULE, ULTRASOUND IMAGING APPARATUS, IMAGE PROCESSING METHOD, AND CONTROL METHOD OF ULTRASOUND IMAGING APPARATUS

CROSS-REFERENCE TO RELATED APPLICATION

This application claims priority from Korean Patent Application No. 10-2013-0081651, filed on Jul. 11, 2013, in the Korean Intellectual Property Office, the disclosure of which is incorporated herein by reference in its entirety.

BACKGROUND

1. Field

Apparatuses and methods consistent with exemplary embodiments relate to an image processing module and an image processing method.

2. Description of the Related Art

Beamforming is performed by focusing data collected over a plurality of channels to estimate the magnitude of reflective waves in a particular space from the data over the plural channels. As such, beamforming may be used in various fields such as, for example, sound navigation and ranging (SONAR), radar, ultrasound imaging, etc.

More specifically, beamforming is performed by appropriately combining data received by each sensor or data input unit and applying a prescribed weight to the combined data to accentuate a particular position signal or relatively attenuate other position signals, thus achieving focusing of ultrasonic signals. In this way, signals and image data suitable for detection or diagnosis of a subject may be acquired.

Beamforming may be classified into data-independent beamforming (or fixed beamforming), and data-dependent beamforming (or adaptive beamforming) according to whether a weight is added to each data used in beamforming. Data-independent beamforming is implemented by applying a predetermined weight to each data regardless of input data. Data-dependant beamforming is implemented by applying different weights to input data. In the data-dependant beamforming, a weight corresponding to input data is determined, and the determined weight is applied to the input data.

Ultrasound imaging apparatuses acquire ultrasound images of a variety of internal tissues of a subject, e.g., a human body, using ultrasound properties. Such ultrasound imaging apparatuses are widely used in various fields including a medical field, etc. because the ultrasound imaging apparatuses may eliminate the risk of X-ray exposure, display images in real time, reduce cost, and occupy a less space than other imaging apparatuses, e.g., magnetic resonance imaging apparatuses. The ultrasound imaging apparatuses beamform ultrasonic signals collected over plural channels to generate ultrasound images.

SUMMARY

One or more exemplary embodiments provide an image processing module, an image processing method, an improved ultrasound imaging apparatus, and a control method of an ultrasound imaging apparatus, in which performance of beamforming may be improved.

One or more exemplary embodiments also provide an image processing module, an ultrasound imaging apparatus, an image processing method, and a control method of an ultrasound imaging apparatus, in an acquired image may have improved image quality, higher resolution, improved signal-to-noise-ratio (SNR) while not increasing or reducing computational load required during beamforming.

In accordance with an aspect of an exemplary embodiment, an image processing module includes an input unit configured to receive a plurality of input signals of a plurality of channels, a weight operator configured to calculate at least one weight to be applied to each channel based on at least one converted signal, wherein the converted signal is acquired by converting at least one input signal among a second plurality of input signals of each channel, or by converting a synthesized input signal of the second plurality of input signals of the each channel, and a synthesizer configured to synthesize the plurality of input signals of the plurality of channels using the at least one weight.

The synthesizer may synthesize the second plurality of input signals of each channel with respect to the plurality of channels, respectively, to generate a plurality of synthesized input signals of the plurality of channels, and resynthesize the plurality of synthesized input signals of the plurality of channels using the at least one weight. The synthesizer may synthesize at least a portion of the plurality of input signals of the plurality of channels using the at least one weight to generate a plurality of synthesized input signals, and resynthesizes the plurality of synthesized input signals.

In accordance with an aspect of another exemplary embodiment, an ultrasound imaging apparatus includes a plurality of ultrasonic elements configured to receive and convert echo ultrasonic waves to output a plurality of ultrasonic signals of plural channels, and a beamformer configured to acquire at least one converted ultrasonic signal by converting at least one ultrasonic signal among a second plurality of ultrasonic signals of each channel, or by converting a synthesized ultrasonic signal of the second plurality of ultrasonic signals of the each channel, configured to calculate at least one weight to be applied to the each channel based on the acquired at least one converted ultrasonic signal, and configured to synthesize the plurality of ultrasonic signals using the at least one weight.

At least one ultrasonic element among the plural ultrasonic elements may emit ultrasonic waves to a subject. More specifically, the plurality of ultrasonic elements may sequentially emit ultrasonic waves to the subject.

In accordance with an aspect of still another exemplary embodiment, an image processing method includes receiving a plurality of input signals of a plurality of channels, calculating at least one weight to be applied to each channel based on at least one converted signal, wherein the at least one converted signal is acquired by converting at least one input signal among a second plurality of plural input signals of the each channel, or by converting a synthesized input signal of the second plurality input signals of the each channel, and synthesizing the plurality of input signals using the at least one weight.

BRIEF DESCRIPTION OF THE DRAWINGS

These and/or other aspects will become more apparent and readily appreciated from the following description of exemplary embodiments, taken in conjunction with the accompanying drawings in which.

DETAILED DESCRIPTION

Figure 1:
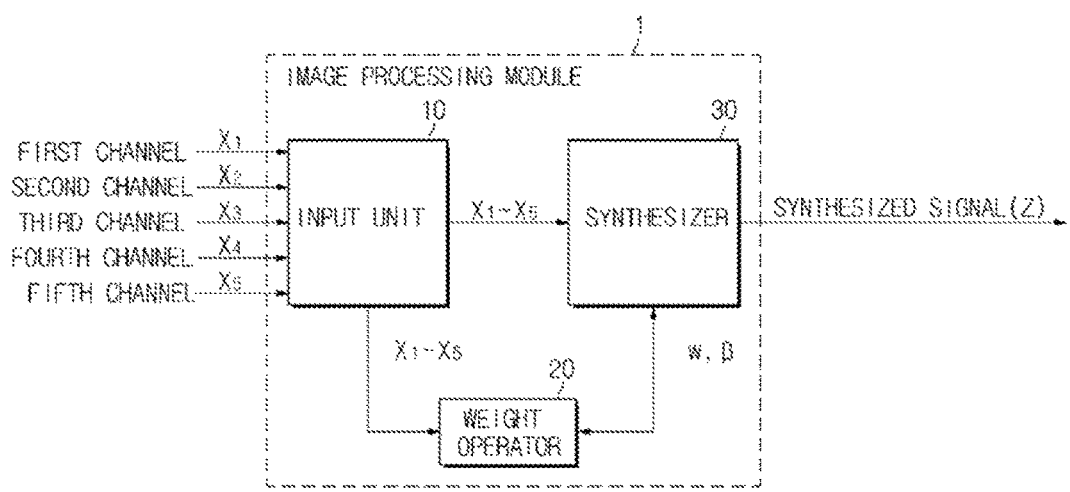
FIG. 1 is a view showing a configuration of an image processing module according to an embodiment.

Hereinafter, exemplary embodiments will now be described more fully with reference to the accompanying drawings. Like reference numerals refer to like elements throughout.

Hereinafter, an image processing module and an image processing method according to an embodiment will be described with reference to FIGS. 1 to 11.

FIG. 1 is a view showing a configuration of an image processing module according to an embodiment.

An image processing module 1 according to an embodiment, as exemplarily shown in FIG. 1, may include an input unit 10, a weight operator 20, and a synthesizer 30.

The input unit 10 receives input signals $x_1$ to $x_5$ of a plurality of channels, i.e., first to fifth channels. The weight operator 20 calculates a weight to be applied to each of the input signals $x_1$ to $x_5$ of the channels. The synthesizer 30 synthesizes the input signals $x_1$ to $x_5$ received by the input unit 10 or converted signals (not shown) of the input signals $x_1$ to $x_5$ using the weight calculated by the weight operator 20, thereby outputting a synthesized signal z.

Figure 2:
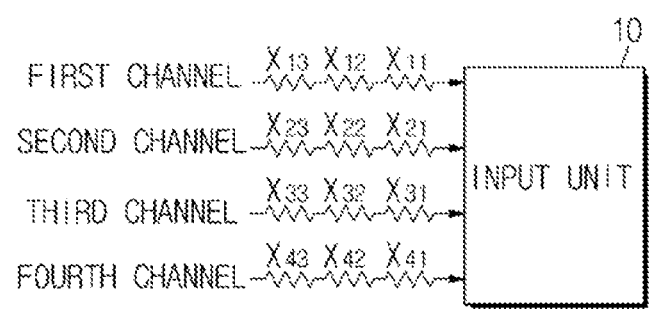
FIG. 2 is an explanatory view of input signals according to an embodiment.

FIG. 2 is an explanatory view of input signals received by the input unit 10 according to an embodiment.

Referring to FIG. 2, the input unit 10 may receive the input signals of a plurality of channels, i.e., first to fourth channels. In this case, the input unit 10 may receive the input signals of the plurality of channels multiple times, respectively. For example, the input unit 10 may receive a plurality of input signals, e.g., input signals $x_{11}$ to $x_{13}$ through at least one channel, e.g., a first channel. Moreover, the input unit 10 may receive plural input signals $x_{11}$ to $x_{13}$, $x_{21}$ to $X_{23}$, $x_{31}$ to $x_{33}$, and $x_{41}$ to $x_{43}$ through each of the first to fourth channels, e.g., first to fourth channels.

In this case, the input signals of each channel, e.g., the input signals $x_{11}$ to $x_{13}$ of the first channel may be sequentially input. In addition, the input signals $x_{11}$ to $x_{43}$ (i.e., $x_{13}$, $x_{21}$ to $x_{23}$, $x_{31}$ to $x_{33}$, $x_{41}$ to $x_{43}$) of the respective channels may be input at a prescribed time interval.

The input signals $x_{11}$ to $x_{43}$ of the respective channels may have a prescribed correlation therebetween according to an input sequence or time of being input to the input unit 10. For instance, the input signal $x_{11}$, which is the first to be input through the first channel, may be related to the input signals $x_{21}$, $x_{31}$, and $x_{41}$, which are the first to be input through other channels, e.g., the second to fourth channels. For instance, the input signals $x_{11}$, $x_{21}$, $x_{31}$, and $x_{41}$, which are the first to be input through the respective channels, may be electrical signals of plural channels generated by different transducers that have received echo sound waves or echo ultrasonic waves reflected by the same target region at the same time.

Referring to FIG. 1, the input signals $x_1$ to $x_5$ received by the input unit 10 are transmitted to the weight operator 20 and the synthesizer 30.

The weight operator 20 may calculate weights ω and β (or an input-signal weight ω and a converted-signal weight β) to be applied to input signals $x_1$ to $x_5$ or converted signals (see u in FIG. 3), and transmit the calculated weights ω and β to the synthesizer 30. Here, the converted signals may be acquired via conversion of the input signals $x_1$ to $x_5$.

According to an embodiment, the weight operator 20 may calculate the input-signal weight ω. The input-signal weight ω may be applied to the input signals $x_1$ to $x_4$ of the respective channels when the input signals $x_1$ to $x_4$ of the plural channels received by the input unit 10 are synthesized. In addition, the input-signal weight ω may be applied to a synthesized input signal (See $x_{1s}$ in FIG. 4) of each channel that is acquired by synthesizing plural input signals of the same channel received by the input unit 10, e.g., the plural input signals $x_{11}$ to $x_{13}$ of the first channel.

Although the input-signal weight ω may be directly calculated from the input signals $x_1$ to $x_5$ by the weight operator 20, the input-signal weight ω may be calculated based on a previously calculated converted-signal weight β.

According to another embodiment, the weight operator 20 may calculate the converted-signal weight β. The converted-signal weight β may be applied to converted signals u of the respective channels when the converted signals u of the input signals $x_1$ to $x_5$ of the plural channels are synthesized (see FIG. 11). In addition, the converted-signal weight β may be applied to synthesized converted signals (See $u_{1s}$ to $u_{5s}$ of FIG. 10). Here, each synthesized converted signal $u_{1s}$ to $u_{5s}$ may be acquired by synthesizing plural input signals of the same channel, e.g., the plural input signals $x_{11}$ to $x_{13}$ of the first channel and converting the synthesized input signal $x_{1s}$ (see FIG. 4). Alternatively, each synthesized converted signal $u_{1s}$ to $u_{5s}$ may be acquired by converting the plural input signals $x_{11}$ to $x_{13}$ of the same channel and synthesizing the plural converted input signals of the same channel.

The synthesizer 30 synthesizes signals transmitted thereto.

The synthesizer 30 may receive plural input signals $x_1$ to $x_5$ of plural channels from the input unit 10, or plural converted signals of plural channels from a converter (See converter 11 in FIG. 3), and synthesize the plural input signals $x_1$ to $x_5$ of the plural channels or the plural converted signals of the plural channels to generate a prescribed synthesized signal z. In addition, the synthesizer 30 may use the input-signal weight ω or the converted-signal weight β generated by the weight operator 20 in synthesizing the signals transmitted thereto.

According to an embodiment, the synthesizer 30 may directly receive the plural input signals $x_1$ to $x_5$ of the plural channels from the input unit 10, and synthesize the plural input signals $x_1$ to $x_5$ of the plural channels to generate the synthesized signal z. In this case, the synthesizer 30 may synthesize the plural input signals $x_1$ to $x_5$ of the plural channels using the input-signal weight ω calculated by the weight operator 20.

According to another embodiment, the synthesizer 30 may synthesize the converted signals u of the plural channels, acquired via conversion of the input signals x, to generate the synthesized signal z. In this case, the synthesizer 30 may synthesize the plural converted signals $u_1$ to $u_4$ of the plural channels using the converted-signal weight β calculated by the weight operator 20.

Figure 3:
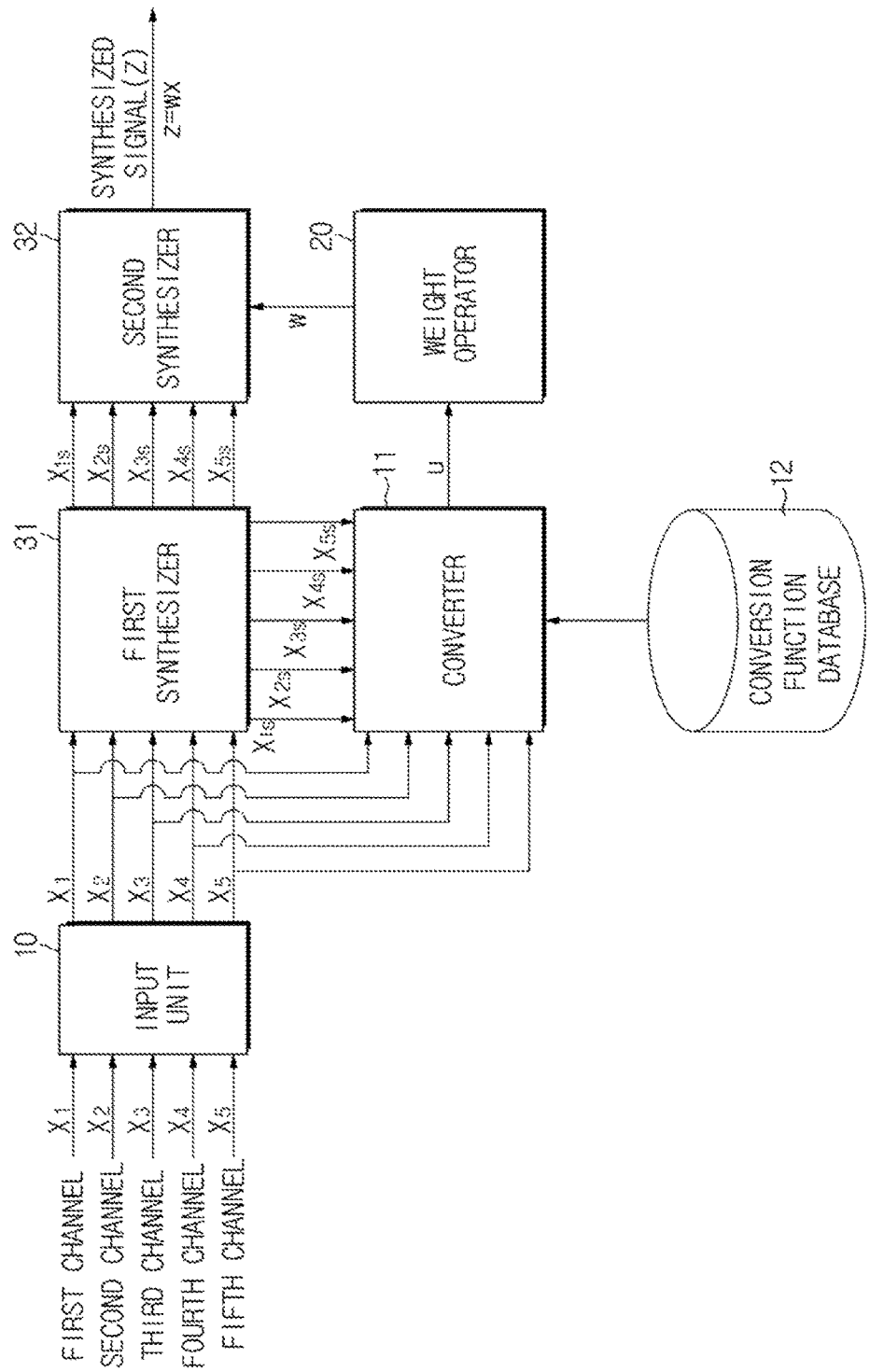
FIG. 3 is a view showing a configuration of an image processing module according to an embodiment.

FIG. 3 is a view showing a configuration of an image processing module according to an embodiment.

As exemplarily shown in FIG. 3, the image processing module 1 according to an embodiment may include the input unit 10, the converter 11, the weight operator 20, a first synthesizer 31, and a second synthesizer 32. In this case, input signals $x_{1s}$ to $x_{5s}$ synthesized by the first synthesizer 31 may be transmitted to the second synthesizer 32.

The input unit 10 may receive plural input signals $x_1$ to $x_5$ of plural channels. The input unit 10 may transmit the plural input signals $x_1$ to $x_5$ of the plural channels to the first synthesizer 31 and the converter 11.

Figure 4:
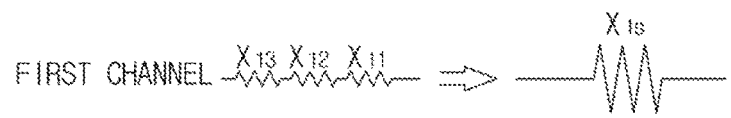
FIGS. 4 and 5 are explanatory views of an operation of a synthesizer according to an embodiment.

FIG. 4 is an explanatory view of an operation of the first synthesizer according to an embodiment.

The first synthesizer 31, as exemplarily shown in FIG. 4, may synthesize plural input signals of the same channel, e.g., input signals $x_{11}$ to $x_{13}$ of the first channel to generate a synthesized input signal $x_{1s}$ of at least one channel. In this case, the first synthesizer 31, for instance, may combine the respective input signals $x_{11}$ to $x_{13}$ of the same channel, without applying a separate weight thereto, to generate the synthesized input signal $x_{1s}$. Alternatively, the first synthesizer 31 may apply a prescribed weight to the respective input signals $x_{11}$ to $x_{13}$ of the same channel, and combine the respective input signals, to which the prescribed weight has been applied, to generate the synthesized input signal $x_{1s}$.

The first synthesizer 31 may synthesize input signals of the same channel among plural input signals $x_{11}$ to $x_{13}$, $x_{21}$ to $x_{23}$, $x_{31}$ to $x_{33}$, and $x_{41}$ to $x_{43}$ of the plural channels shown in FIG. 2, e.g., the first to fourth channels to generate synthesized input signals $x_{1s}$ to $x_{4s}$ of the plural channels.

According to an embodiment, the first synthesizer 31 may receive plural input signals $x_{11}$ to $x_{55}$ (not shown) of plural channels from the input unit 10, and synthesize the input signals of the same channel to output synthesized input signals $x_{1s}$ to $x_{5s}$.

As exemplarily shown in FIG. 3, according to an embodiment, the synthesized input signals $x_{1s}$ to $x_{5s}$ of the first synthesizer 31 may be transmitted to the second synthesizer 32. In addition, according to an embodiment, the synthesized input signals $x_{1s}$ to $x_{5s}$ may be transmitted to the converter 11.

Figure 5:
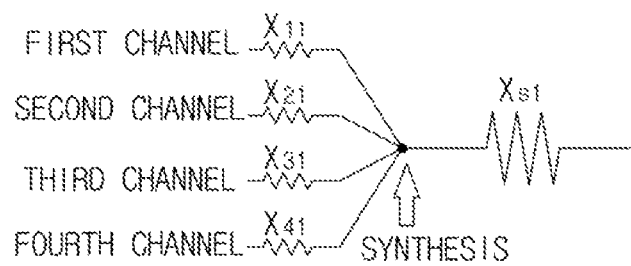

FIG. 5 is an explanatory view of an operation of the second synthesizer according to an embodiment.

The second synthesizer 32, as exemplarily shown in FIG. 5, may synthesize plural input signals of different channels, e.g., input signals $x_{11}$ to $x_{41}$ to generate a synthesized input signal $x_{s1}$. In this case, the plural input signals $x_{11}$ to $x_{41}$ to be synthesized may have a correlation therebetween. For instance, the input signals may be electrical signals of plural channels generated by sound waves, ultrasonic waves, and microwaves that are reflected by the same target region at the same time. The second synthesizer 32, for instance, may combine the input signals $x_{11}$ to $x_{41}$ of different channels without separate processing to generate the synthesized input signal $x_{s1}$. Alternatively, the second synthesizer 32 may apply a prescribed weight to respective channels, and combine the input signals $x_{11}$ to $x_{41}$ of the respective channels, to which the prescribed weight has been added, to generate the synthesized input signal $x_{s1}$.

According to an embodiment, the image processing module 1, as exemplarily shown in FIG. 3, may further include the converter 11 configured to convert signals.

The converter 11 may convert input signals x of plural channels or the synthesized input signals $x_{1s}$ to $x_{5s}$ of the input signals $x_1$ to $x_5$ of the respective channels to acquire converted signals u of at least one channel.

According to an embodiment, the converter 11 may receive plural input signals x of plural channels from the input unit 10, and acquire converted signals u of at least one channel from the plural input signals x of the plural channels using a prescribed conversion function V. According to another embodiment, the converter 11, as exemplarily shown in FIG. 3, may receive the synthesized input signals $x_{1s}$ to $x_{5s}$ from the first synthesizer 31, and apply a prescribed conversion function V to the synthesized input signals $x_{1s}$ to $x_{5s}$ to generate converted signals u of at least one channel with respect to the synthesized input signals $x_{1s}$ to $x_{5s}$.

A procedure of converting the input signals x or the synthesized input signals $x_{1s}$ to $x_{5s}$ using the conversion function V by the converter 11 may be represented by the following Equation 1.

$$u = V^H x \qquad \text{Equation 1}$$

Here, x is an input signal or synthesized input signal, and V is a prescribed conversion function. Also, u is a converted signal that is acquired by converting the input signal or synthesized input signal x using the prescribed conversion function V.

According to an embodiment, the input signal or synthesized input signal x and the converted signal u may be expressed by an (A×B) matrix. Here, A and B are positive integers. When B is 1, the input signal x and the converted signal u are expressed by an (A×1) matrix. For example, the input signal x and the converted signal u may be represented by the following Equation 2 and Equation 3, respectively.

$$x = \begin{pmatrix} x_1 \\ x_2 \\ \ldots \\ x_m \end{pmatrix} \qquad \text{Equation 2}$$

$$u = \begin{pmatrix} u_1 \\ u_2 \\ \ldots \\ u_n \end{pmatrix} \qquad \text{Equation 3}$$

Here, m and n are positive integers.

When the input signal or synthesized input signal x and the converted signal u are represented by Equation 2 and Equation 3, the input signal or synthesized input signal x has a dimension of m, and the converted signal u has a dimension of n.

Here, the dimension of the input signal or synthesized input signal x may be defined by the number of channels of the input signal or synthesized input signal x. The dimension of the converted signal u may be defined by the number of channels of the converted signal u. In addition, each element of a matrix with respect to the input signals x of Equation 2, e.g., $x_m$ may mean an input signal of an $m^{th}$ channel or a synthesized input signal of the $m^{th}$ channel. Likewise, each element of a matrix with respect to the converted signals u of Equation 3, e.g., $u_n$ may mean a converted signal of an $n^{th}$ channel acquired via conversion of input signals of the $n^{th}$ channel. It will be appreciated that the respective elements $x_1$ to $x_m$ of the input signals x and the respective elements $u_1$ to $u_n$ of the converted signals u may be represented in a prescribed matrix form, e.g., a (1×a) matrix.

The conversion function V is a prescribed function to convert the input signals x or the synthesized input signals $x_{1s}$ to $x_{5s}$ of the respective channels into the converted signals u.

According to an embodiment, the conversion function V may include at least one basis vector or a combination of plural basis vectors. In this case, the plural basis vectors constituting the conversion function V may be substantially perpendicular to one another. In this case, the plural basis vectors may be, e.g., eigenvectors, or Fourier basis vectors. Various basis vectors, such as the eigenvectors or Fourier basis vectors, stored in a conversion function database 12 may be provided to the converter 11.

The at least one basis vector or the plural basis vectors of the conversion function V may be acquired via main element analysis with respect to an appropriate (e.g., optimum) value of the input-signal weight ω that is to be applied to the input signals x according to minimum variance.

The image processing module 1 according to an embodiment, as exemplarily shown in FIG. 3, may further include the conversion function database 12 in which the conversion function V or at least one basis vector used to generate the conversion function V is stored. According to an embodiment, at least one conversion function V of the conversion function database 12 may be previously calculated based on various input signals x or synthesized input signals $x_s$ that may be acquired, e.g., empirically or theoretically. In addition, the conversion function database 12 may include at least one basis vector to generate the conversion function V.

The converter 11 according to an embodiment, as exemplarily shown in FIG. 3, may read the conversion function database 12, and select and call at least one conversion function V from the conversion function database 12. In this case, the converter 11 may select and call an appropriate conversion function V according to the input signals x or the synthesized input signals $x_{1s}$ to $x_{5s}$, or may select and call an arbitrary conversion function v regardless of the input signals x or the synthesized input signals $x_{1s}$ to $x_{5s}$. In addition, the converter 11 may always call the same conversion function V. The converter 11 may convert the input signals x or the synthesized input signals $x_{1s}$ to $x_{5s}$ into the converted signals u using the called conversion function V. For example, the conversion function V called by the converter 11 may be determined according to preset system settings or user selection.

The converter 11 may call at least one basis vector from the conversion function database 12 when the conversion function database 12 stores the at least one basis vector used to generate the conversion function V. In this case, the converter 11 may generate at least one conversion function V via combination of the called at least one basis vector, and convert the input signals x or the synthesized input signals $x_{1s}$ to $x_{5s}$ using the generated at least one conversion function V. To generate the at least one conversion function V, the converter 11 may call an appropriate basis vector according to the input signals x or the synthesized input signals $x_{1s}$ to $x_{5s}$, or may call an arbitrary basis vector or only the same basis vector regardless of the input signals x or the synthesized input signals $x_{1s}$ to $x_{5s}$. In addition, the converter 11 may select at least one basis vector among plural basis vectors stored in the conversion function database 12 according to preset settings of a system equipped with the image processing module 1 or selection of a user who uses the system, and determine the conversion function V via combination of the selected plural basis vectors.

It will be appreciated that the converter 11 may convert the input signals x or the synthesized input signals $x_{1s}$ to $x_{5s}$ into the converted signals u using a predefined conversion function V, thereby obviating a need for search the conversion function database 12.

The converted signals u, converted by the converter 11, as exemplarily shown in FIG. 3, may be transmitted to the weight operator 20. In this case, the weight operator 20 according to an embodiment may calculate the input-signal weight ω using the converted signals u.

Figure 6:
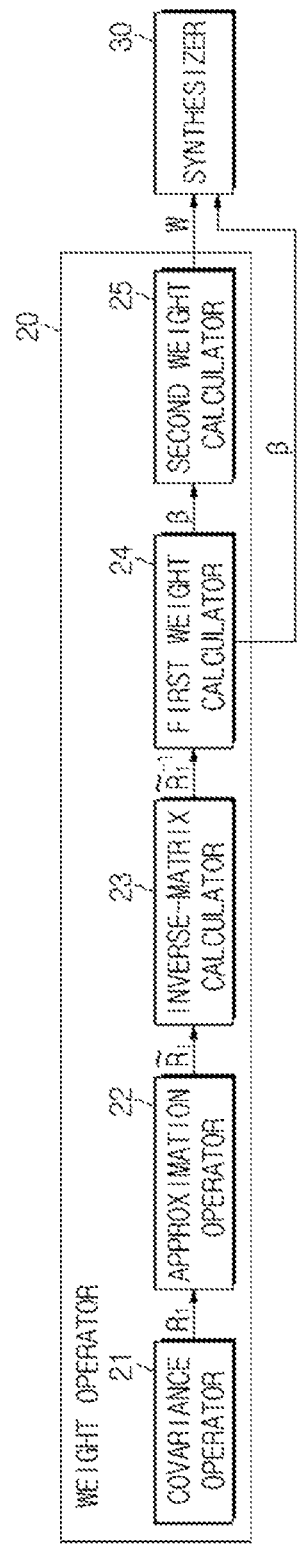
FIG. 6 is a block diagram of a weight operator according to an embodiment.

FIG. 6 is a block diagram of the weight operator according to an embodiment.

Referring to FIG. 6, the weight operator 20 may include a covariance operator 21, an approximation operator 22, an inverse-matrix calculator 23, and a first weight calculator 24, for calculation of a weight. According to an embodiment, the weight operator 20 may further include a second weight calculator 25.

The covariance operator 21 implements covariance calculation on the converted signals u acquired via conversion of the input signals x. Covariance may be calculated according to the following Equation 4.

$$R = E(XX^H) \qquad \text{Equation 4}$$

When the converted signals u are input to the weight operator 20, the covariance operator 21 implements covariance calculation according to the following Equation 5.

$$R_1 = E[u \cdot u^H] \qquad \text{Equation 5}$$

Here, $R_1$ is covariance, and u is the converted signal.

Alternatively, when the input signals x are input to the weight operator 20, the covariance operator 21 may implement covariance calculation according to the following Equation 6.

$$R_1 = E[V^H x \cdot x^H V] \qquad \text{Equation 6}$$

Here, $R_1$ is covariance, V is the above-described conversion function, and x is the input signal. When substituting the above-described Equation 1 into Equation 6, as exemplarily shown in the following Equation 7, covariance calculation using the input signals x and Equation 6 is equal to covariance calculation using the converted signals u described in Equation 5.

$$\begin{aligned} R_1 &= E[V^H x \cdot x^H V] \\ &= E[u \cdot u^H] \end{aligned} \qquad \text{Equation 7}$$

The covariance $R_1$ calculated using the converted signals u by the covariance operator 21 is transmitted to the approximation operator 22. The approximation operator 22 may calculate an approximate value of the covariance $R_1$. According to an embodiment, to calculate the approximate value of the covariance $R_1$, the approximation operator 22 may generate an approximate matrix in the form of a Toeplitz matrix based on the covariance $R_1$ expressed in a matrix form.

The Toeplitz matrix is a matrix in which all diagonal elements have the same value. The Toeplitz matrix provides easy calculation of an inverse-matrix and requires less computational load than other matrices when calculating the inverse-matrix using an information processing device. Thus, faster inverse-matrix calculation may be accomplished.

The covariance operator 21 acquires a Toeplitz matrix approximate to the covariance $R_1$ using the following Equation 8.

$$\tilde{R}_{1,m} = \frac{1}{L-m} \sum_{l=1}^{L-m} R_{1,l,l+m}(m=0, 1, \ldots, L-1) \quad \text{Equation 8}$$

Here, $R_{1,l,l+m}$ is an element at an $l^{th}$ row and an $m^{th}$ column of the covariance $R_1$. L is the number of rows of the covariance $R_1$ with respect to the converted signals u.

When $\tilde{R}_{1,m}$ is acquired according to Equation 8, $\tilde{R}_{1,m}$ is input to an $m^{th}$ diagonal line of an approximate matrix $\tilde{R}_1$ of the covariance $R_1$. As a result, an approximate matrix $\tilde{R}_1$ via Toeplitz approximation of the covariance $R_1$ may finally be acquired.

The approximate matrix $\tilde{R}_1$ calculated by the approximation operator 22 is transmitted to the inverse-matrix calculator 23. The inverse-matrix calculator 23 calculates an inverse-matrix $\tilde{R}_1^{-1}$ of the approximate matrix $\tilde{R}_1$.

The inverse-matrix $\tilde{R}_1^{-1}$ calculated by the inverse-matrix calculator 23 is transmitted to the first weight calculator 24. The first weight calculator 24 calculates a converted-signal weight $\beta$ based on the transmitted inverse-matrix $\tilde{R}_1^{-1}$ of the approximate matrix $\tilde{R}_1$. The first weight calculator 24, according to an embodiment, may calculate the converted-signal weight $\beta$ according to the following Equation 9.

$$\beta = \frac{\tilde{R}_1^{-1} v_1}{v_1^H \tilde{R}_1^{-1} v_1} \quad \text{Equation 9}$$

Here, $\beta$ is the calculated converted-signal weight, $\tilde{R}_1^{-1}$ Is an inverse-matrix of the approximate matrix $\tilde{R}_1$ calculated by the inverse-matrix calculator 23, and $v_1$ is a steering vector.

The steering vector $v_1$ serves to control a signal phase. According to an embodiment, the steering vector $v_1$ of Equation 9 may be a vector converted by a prescribed conversion function. In this case, the conversion function for conversion of the steering vector $v_1$ may be equal to the conversion function V used to convert the input signals x. More specifically, the converted steering vector $v_1$ may be calculated using the following Equation 10.

$$v_1 = V^H \alpha \quad \text{Equation 10}$$

Here, $\alpha$ is a predefined steering vector before conversion, and $v_1$ is a converted steering vector.

The converted-signal weight $\beta$ calculated by the above-described Equation 9 may vary according to the input signals x, and may also vary according to the conversion function V used by the covariance operator 21. In this case, since the conversion function V may be selected among a plurality of conversion functions V previously calculated and defined according to the input signals x, the converted-signal weight $\beta$ mainly varies according to the input signals x.

The converted-signal weight $\beta$ may be a prescribed column vector. When the conversion function V is expressed as an (M×N) matrix, the converted-signal weight $\beta$ is given as an (N×1) matrix, i.e. an (N×1) column vector.

The calculated converted-signal weight $\beta$, as exemplarily shown in FIG. 6, may be transmitted to the second weight calculator 25, or may be transmitted to the synthesizer 30.

When the input unit 10 transmits the input signals $x_1$ to $x_5$ to the first synthesizer 31 as exemplarily shown in FIG. 3, the first weight calculator 24 may transmit the calculated converted-signal weight $\beta$ to the second weight calculator 25 to enable calculation of the input-signal weight $\omega$ that is a weight to be applied to each channel of the input signals $x_1$ to $x_5$ or the synthesized input signals $x_{1s}$ to $x_{5s}$.

When the first weight calculator 24 transmits the converted-signal weight $\beta$ to the second weight calculator 25, the second weight calculator 25 calculates the input-signal weight $\omega$ based on the transmitted converted-signal weight $\beta$. The input-signal weight $\omega$ may be calculated via combination of the prescribed conversion function V and the converted-signal weight $\beta$ calculated by the first weight calculator 24. For instance, the second weight calculator 25 may calculate the input-signal weight $\omega$ via combination of the conversion function V, used by the converter 11 and/or the covariance operator 21, and the converted-signal weight $\beta$. Thus, the input-signal weight $\omega$ may be represented by the following Equation 11.

$$\omega = V\beta \quad \text{Equation 11}$$

The calculated input-signal weight $\omega$ may be an optimum weight for beamforming of the input signals. Assuming that the input-signal weight $\omega$ is an optimum value for the input signals, it will be appreciated from Equation 11 that the converted-signal weight $\beta$ is a weight to be applied to at least one conversion function V for calculation of the optimum value of the input-signal weight $\omega$ for the input signals.

The calculated input-signal weight $\omega$ may be transmitted to the second synthesizer 32 as exemplarily shown in FIG. 3.

The second synthesizer 32 synthesizes the transmitted signals of plural channels using the input-signal weight $\omega$ transmitted from the weight operator 20. Referring to FIG. 3, the second synthesizer 32 implements synthesis of the synthesized input signals $x_{1s}$ to $x_{5s}$ of the plural channels from the first synthesizer 31.

Figure 7:
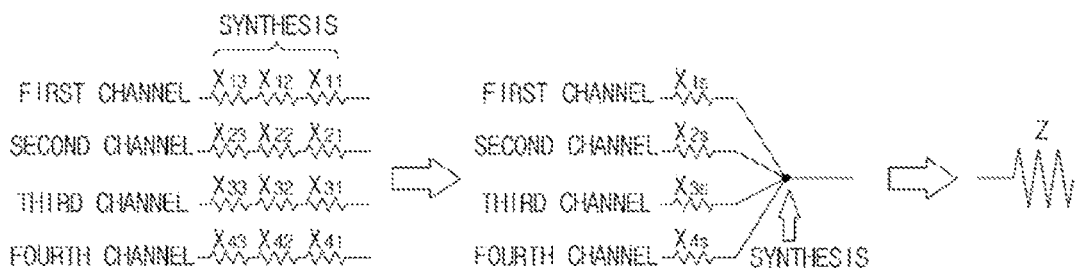
FIG. 7 is an explanatory view of an operation of a synthesizer according to another embodiment.

FIG. 7 is another explanatory view of a synthesis operation according to an embodiment.

As exemplarily shown in FIG. 7, according to an embodiment, to synthesize plural input signals $x_{11}$ to $x_{13}$, $x_{21}$ to $x_{23}$, $x_{31}$ to $x_{33}$, and $x_{41}$ to $x_{43}$ of plural channels, first to fourth channels, plural input signals input through the same channel may be first synthesized. For instance, the plural input signals $x_{11}$ to $x_{13}$ input through the first channel may be synthesized to generate a synthesized input signal $x_{1s}$ of the first channel. As a result, synthesized input signals $x_{1s}$ to $x_{4s}$ for respective channels are acquired. This may be implemented by the above-described first synthesizer 31. Subsequently, the synthesized input signals $x_{1s}$ to $x_{4s}$ of the plural channels, synthesized on a per channel basis, may again be synthesized as exemplarily shown in FIG. 8, which will be described later. As a result, at least one synthesized signal z is generated.

In this case, a prescribed weight, e.g., the input-signal weight ω transmitted from the weight operator 20 is applied to each channel to enable synthesis of the synthesized input signals $x_{1s}$ to $x_{4s}$. More specifically, the synthesized input signals $x_{1s}$ to $x_{4s}$ of the plural channels, synthesized on a per channel basis, are multiplied by the input-signal weight ω as exemplarily shown in the following Equation 12 to generate at least one synthesized signal z, as exemplarily shown in FIG. 7.

$$Z=\omega X \quad \text{Equation 12}$$

Here, X is a variable constituted of the corresponding input signals $x_{11}$ to $x_{41}$ of different channels or the synthesized input signals $x_{1s}$ to $x_{5s}$ acquired by the first synthesizer 31. The synthesis according to Equation 12 may be implemented by the above-described second synthesizer 32.

Figure 8:
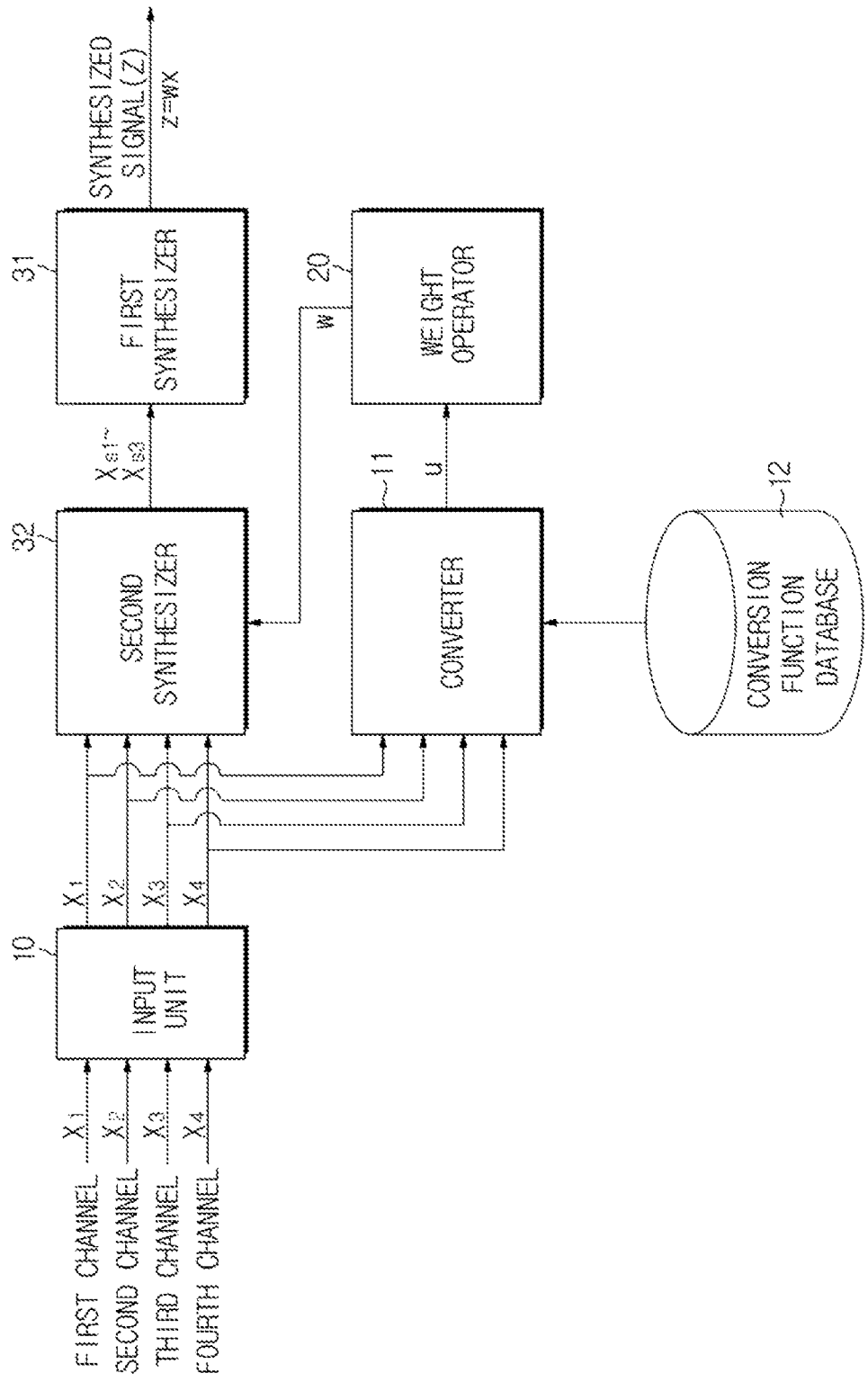
FIG. 8 is a view showing a configuration of an image processing module according to another embodiment.

FIG. 8 is a view showing a configuration of an image processing module according to another embodiment.

Referring to FIG. 8, the image processing module 1 according to another embodiment may include the input unit 10, the converter 11, the weight operator 20, the first synthesizer 31, and the second synthesizer 32. Input signals $x_{s1}$ to $x_{s3}$ synthesized by the second synthesizer 32 may be transmitted to the first synthesizer 31. In this case, input signals $x_{11}$ to $x_{41}$ (See FIG. 9) of different channels related to one another are first synthesized, and plural synthesized input signals $x_{s3}$ to $x_{s1}$ may again be synthesized.

The input unit 10 may receive plural input signals $x_1$ to $x_4$ of plural channels, and transmit the same to the second synthesizer 32 and the converter 11.

The converter 11 converts input signals $x_1$ to $x_4$ of plural channels to generate converted signals u of at least one channel. In this case, the converter 11 may convert the input signals $x_1$ to $x_4$ of the plural channels using a prescribed conversion function V. According to an embodiment, the converter 11 may call the prescribed conversion function V from the conversion function database 12, and convert the input signals $x_1$ to $x_4$ of the plural channels using the called conversion function V. The generated converted-signals u may be transmitted to the weight operator 20.

The weight operator 20 may calculate an input-signal weight ω using the transmitted converted-signals u. To this end, the weight operator 20, as exemplarily shown in FIG. 6, may include the covariance operator 21, the approximation operator 22, the inverse-matrix calculator 23, the first weight calculator 24, and the second weight calculator 25, for calculation of the input-signal weight ω. The weight operator 20 may receive the prescribed conversion function V or related information from the converter 11. The input-signal weight ω generated by the weight operator 20 is transmitted to the second synthesizer 32.

Figure 9:
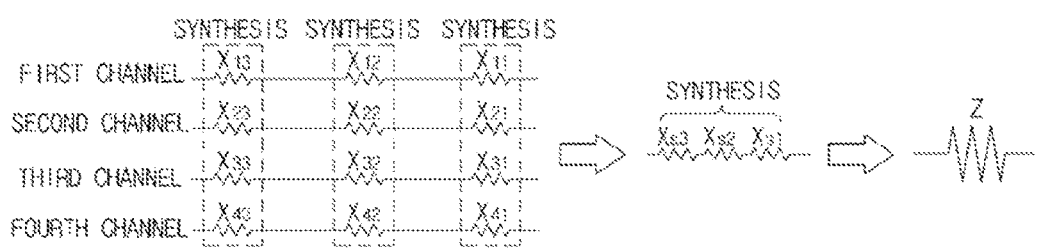
FIG. 9 is an explanatory view of an operation of a synthesizer according to still another embodiment.

FIG. 9 is an explanatory view of a synthesis operation according to still another embodiment.

As exemplarily shown in FIG. 9, according to an embodiment, corresponding input signals $x_{11}$ to $x_{41}$ of different channels, i.e., first to fourth channels, among plural input signals $x_{11}$ to $x_{43}$, i.e., $x_{11}$, $x_{12}$, $x_{13}$ from the first channel, $x_{21}$, $x_{22}$, $x_{23}$ from the second channel, $x_{31}$, $x_{32}$, $x_{33}$ from the third channel, and $x_{41}$, $x_{42}$, and $x_{43}$ from the fourth channel may first be synthesized. For instance, the input signals $x_{11}$ to $x_{41}$ of the respective first to fourth channels may first be synthesized to generate a synthesized input signal $x_{s1}$. In other words, as exemplarily shown in FIG. 9, sequentially input signals $x_{11}$ to $x_{43}$ of the plural channels are synthesized to acquire plural synthesized input signals $x_{s1}$ to $x_{s3}$.

In this case, the input signals $x_{11}$ to $x_{41}$ of respective channels may be synthesized using a prescribed weight, e.g., the input-signal weight ω applied to each channel. The input-signal weight ω may be calculated and transmitted by the weight generator 20. In this case, the above-described Equation 12 may be used. It is noted that in Equation 12, Z is not a synthesized signal, but a synthesized input signal $x_{s1}$. When the input signals $x_{11}$ to $x_{41}$ of the respective channels are ultrasonic signals collected by an ultrasonic probe of an ultrasound imagining apparatus, the above-described synthesis may correspond to a process in which ultrasonic signals of plural channels are focused using a beamforming coefficient to synthesize an ultrasound image.

The above-described synthesis may be implemented by the second synthesizer 32.

The second synthesizer 32, as exemplarily shown in FIG. 8, may receive the plural input signals $x_{11}$ to $x_{43}$ of the plural channels from the input unit 10, and synthesize the plural input signals $x_{11}$ to $x_{43}$ of the plural channels using the input-signal weight ω. As a result, the second synthesizer 32 may output plural synthesized input signals $x_{s1}$ to $x_{s3}$ of at least one channel. The plural input signals $x_{s1}$ to $x_{s3}$ synthesized by the second synthesizer 32 may be transmitted to the first synthesizer 31 as exemplarily shown in FIG. 8.

As the plural synthesized input signals $x_{s1}$ to $x_{s3}$ are again synthesized as exemplarily shown in FIG. 9, a synthesized signal z is generated. In this case, all of the synthesized input signals $x_{s1}$ to $x_{s3}$ may again be synthesized without applying a separate weight to generate the synthesized signal z. Alternatively, a prescribed weight may be applied to each of the synthesized input signals $x_{s1}$ to $x_{s3}$, such that the synthesized input signals $x_{s1}$ to $x_{s3}$ may again be synthesized using the prescribed weight to generate the synthesized signal z.

The above-described synthesis may be implemented by the first synthesizer 31.

The first synthesizer 31 receives the plural synthesized input signals $x_{s1}$ to $x_{s3}$ from the second synthesizer 32, and implements synthesis of the plural synthesized input signals $x_{s1}$ to $x_{s3}$ to generate at least one synthesized signal z.

Figure 10:
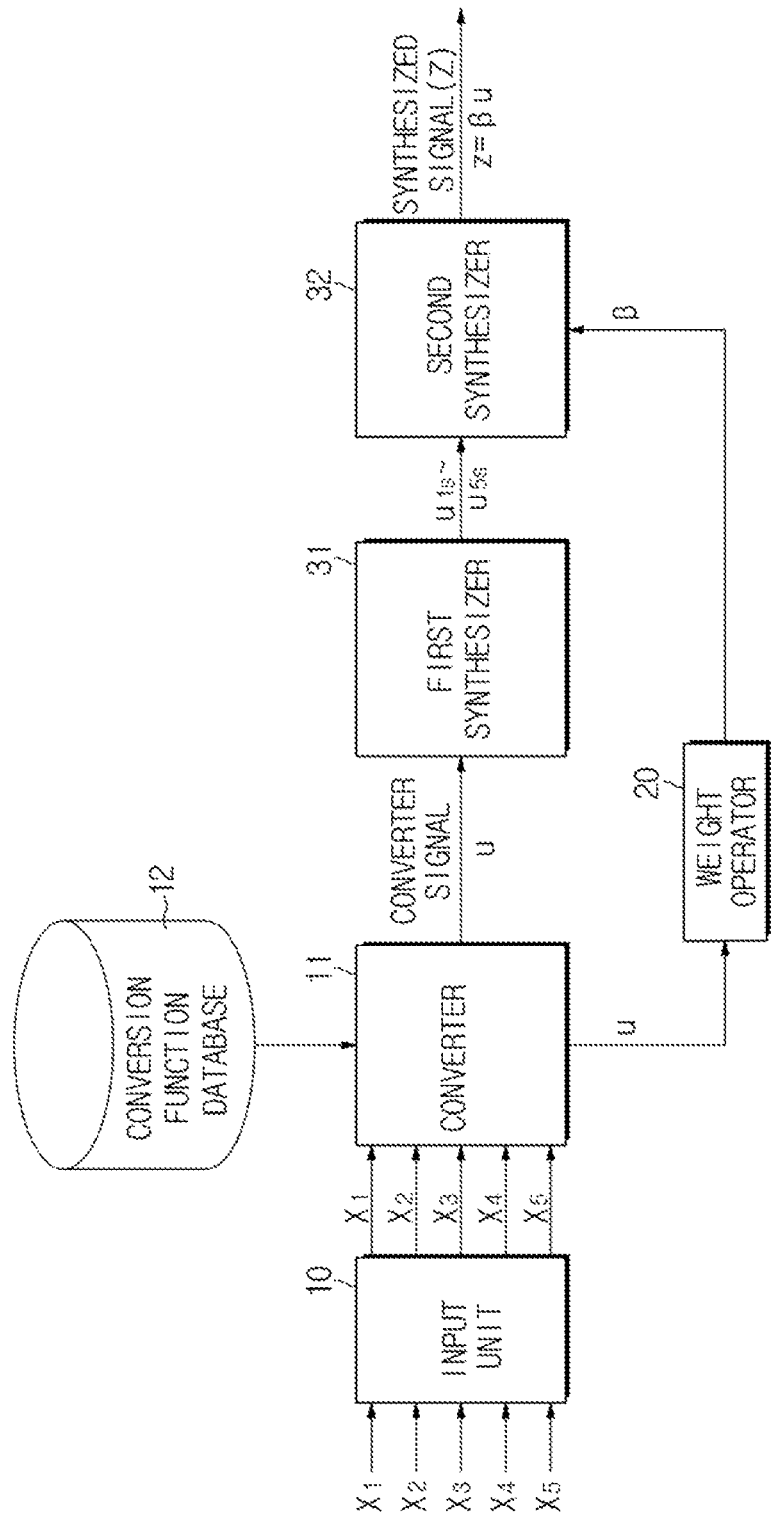
FIGS. 10 and 11 are views showing a configuration of an image processing module according to still other embodiments.

FIG. 10 is a view showing a configuration of an image processing module according to still another embodiment.

Referring to FIG. 10, the image processing module 1 according to another embodiment includes the input unit 10, the converter 11, the weight operator 20, the first synthesizer 31, and the second synthesizer 32. Input signals $x_1$ to $x_5$ from the input unit 10 may be transmitted to the converter 11 and not transmitted to the first synthesizer 31. In this case, the converter 11 may transmit converted signals u generated based on the input signals $x_1$ to $x_5$ to the weight operator 20 as well as the first synthesizer 31.

The input unit 10, as exemplarily shown in FIG. 10, may receive plural input signals $x_1$ to $x_5$ of plural channels, and transmit the received plural input signals $x_1$ to $x_5$ of the plural channels to the converter 11.

The converter 11 converts the plural input signals $x_1$ to $x_5$ of the plural channels to generate plural converted signals u of at least one channel. In this case, the converter 11 may convert the input signals $x_1$ to $x_5$ of the plural channels using a prescribed conversion function V. According to an embodiment, the converter 11 may call the predetermined conversion function V from the conversion function database 12, and convert the input signals $x_1$ to $x_5$ of the plural channels using the called conversion function V. The converter 11 may transmit the generated converted signals u to the weight operator 20 and the first synthesizer 31.

The weight operator 20 receives the converted signals u. Also, the weight operator 20 may further receive the prescribed conversion function V or related information from the converter 11.

The weight operator 20 may calculate a converted-signal weight β using the transmitted converted signals u. Referring again to FIG. 6, the weight operator 20 may include the covariance operator 21, the approxmation operator 22, the inverse-matrix calculator 23, and the first weight calculator 24, and calculate the converted-signal weight β using the aforementioned components. Once the converted-signal weight β is calculated, as exemplarily shown in FIGS. 6 and 10, the first weight calculator 24 of the weight operator 20 transmits the converted-signal weight β to the synthesizer 30, and more particularly, to the second synthesizer 32. In this case, the calculated converted-signal weight β needs not be transmitted to the second weight calculator 25.

The first synthesizer 31 receives the plural converted signals u of at least one channel from the converter 11. The first synthesizer 31 synthesizes the plural converted signals u of the at least one channel. More specifically, the first synthesizer 31 synthesizes plural converted signals u of the same channel among the transmitted plural converted signals u of the at least one channel, in a similar manner as exemplarily shown in FIG. 4 or FIG. 7, to generate synthesized converted signals $u_{1s}$ to $u_{5s}$ of the at least one channel. The first synthesizer 31 transmits the synthesized converted signals $u_{1s}$ to $u_{5s}$ of the at least one channel to the second synthesizer 32.

The second synthesizer 32 may implement synthesis of the synthesized converted signals $u_{1s}$ to $u_{5s}$ of the at least one channel, transmitted from the first synthesizer 31, to output at least one synthesized signal z. More specifically, the second synthesizer 32 may again synthesize the synthesized converted signals $u_{1s}$ to $u_{5s}$ of different channels, in a similar manner as exemplarily shown in FIG. 5, to generate at least one synthesized signal z.

The second synthesizer 32, for instance, may combine the converted signals $u_{1s}$ to $u_{5s}$ of the different channels without separate processing to generate the synthesized signal z. Alternatively, the second synthesizer 32 may apply a prescribed weight to each channel, and combine the converted signals $u_{1s}$ to $u_{5s}$ of the respective channels to which the prescribed weight has been applied, to generate the synthesized signal z. In this case, the prescribed weight may be the converted-signal weight β.

When the synthesized converted signal $u_{1s}$ of one of the plural channels is transmitted to the second synthesizer 32, the second synthesizer 32 may not perform a separate synthesis process.

When the first synthesizer 31 or the second synthesizer 32 directly or indirectly receives the converted signals u from the converter 11 as exemplarily shown in FIG. 10, the second synthesizer 32 may multiply plural corresponding synthesized converted signals u of different channels by the converted-signal weight β as represented in the following Equation 13, to generate the synthesized signal z or the synthesized input signals $X_{s1}$ to $x_{s4}$.

$$z = \beta u \quad \text{Equation 13}$$

Here, Z is the synthesized signal, β is the converted-signal weight, and u is the converted signals or the converted signals $u_{1s}$ to $u_{5s}$ synthesized by the first synthesizer 31.

The synthesized signal z according to Equation 12 and the synthesized signal z according to Equation 13 may be substantially the same. In other words, the synthesized signal z, which is acquired by multiplying the input-signal weight ω calculated by the weight operator 20 by the input signals $x_1$ to $x_5$, synthesized by the first synthesizer 31, may be substantially equal to the synthesized signal z, which is acquired by multiplying the converted-signal weight β calculated by the weight operator 20 by the converted signals $u_{1s}$ to $u_{5s}$ synthesized by the first synthesizer 31. This may be proved as represented by the following Equation 14.

$$\begin{aligned} Z &= \beta^H u \\ &= \beta^H V^H x \\ &= (V\beta)^H x \\ &= w^H x \end{aligned} \quad \text{Equation 14}$$

Figure 11:
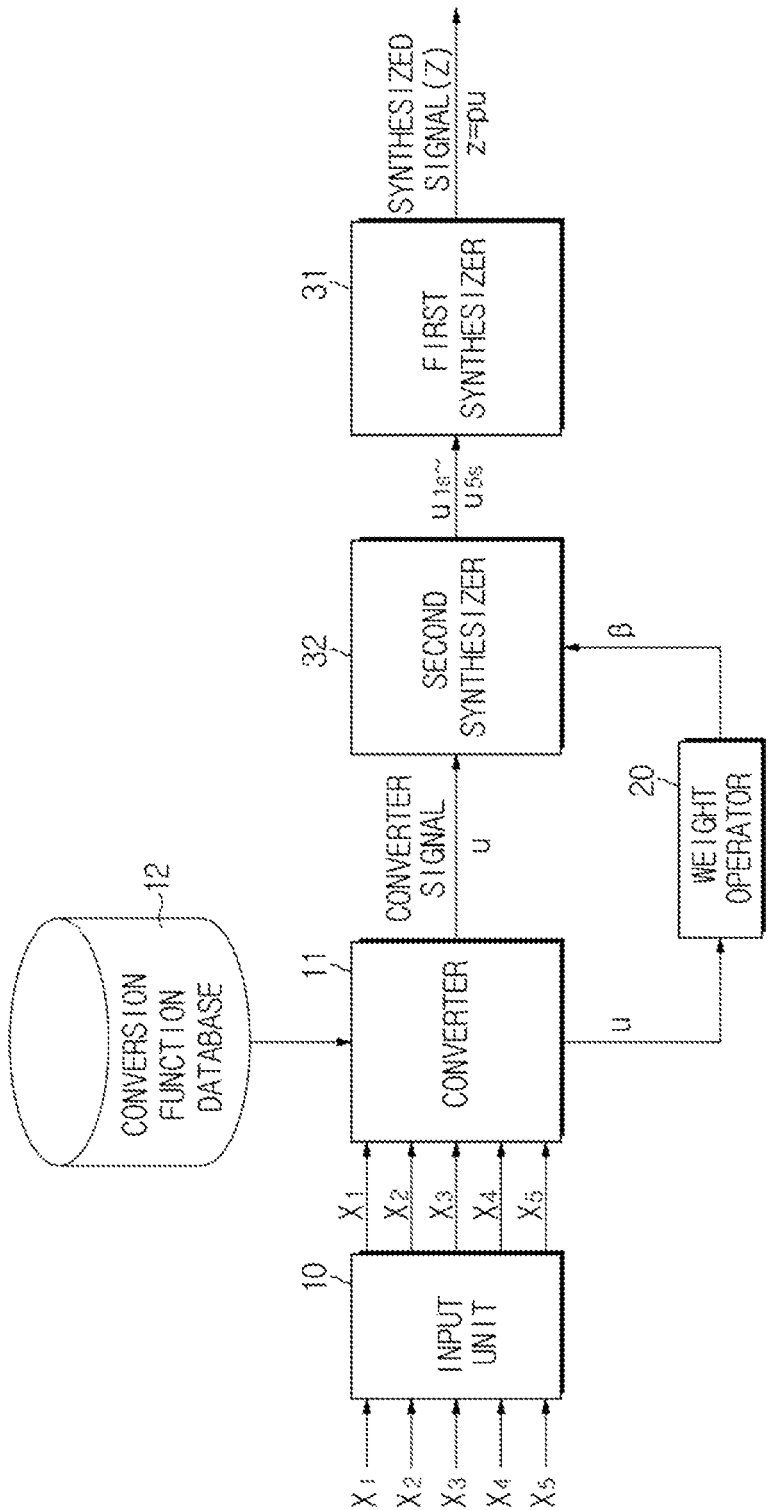

FIG. 11 is a view showing a configuration of an image processing module according to still another embodiment.

Referring to FIG. 11, the image processing module 1 according to another embodiment includes the input unit 10, the converter 11, the weight operator 20, the first synthesizer 31, and the second synthesizer 32. In a similar manner as in the above-description of FIG. 10, input signals $x_1$ to $x_5$ from the input unit 10 may be transmitted to the converter 11 and not transmitted to the first synthesizer 31. In this case, differently from the embodiment of FIG. 10, the converter 11 may transmit converted signals u to the weight operator 20 and the second synthesizer 32.

The input unit 10 may receive plural input signals $x_1$ to $x_5$ of plural channels, e.g., first to fifth channels, and transmit the received plural input signals $x_1$ to $x_5$ of the plural channels to the converter 11.

The converter 11 converts the plural input signals $x_1$ to $x_5$ of the plural channels to generate plural converted signals u of at least one channel. In a similar manner as in the above description, the converter 11 may convert the input signals $x_1$ to $x_5$ of the plural channels using a prescribed conversion function V. In addition, the converter 11 may acquire a predetermined conversion function V from the conversion function database 12 to generate the plural converted signals u of at least one channel. The converter 11 transmits the generated converted signals u to the weight operator 20 and the second synthesizer 32.

The weight operator 20 may receive the converted signals u, and calculate the converted-signal weight β using the converted signals u. More specifically, as exemplarily shown in FIG. 6, the weight operator 20 may include the covariance operator 21, the approxmation operator 22, the inverse-matrix calculator 23, and the first weight calculator 24. The weight operator 20 may calculate the converted-signal weight β using the aforementioned components. Once the converted-signal weight β is calculated, the first weight calculator 24 of the weight operator 20 transmits the calculated converted-signal weight β to the synthesizer 30, and more particularly to the second synthesizer 32 as exemplarily shown in FIGS. 6 and 11.

The second synthesizer 32 may synthesize the plural converted signals u of the at least one channel transmitted from the converter 11 to generate at least one synthesized converted signal $u_{1s}$ to $u_{5s}$. More specifically, the second synthesizer 32, as exemplarily shown in FIG. 5, may synthesize the converted signals u of different channels to generate at least one synthesized converted signal $u_{1s}$ to $u_{5s}$. In this case, the converted signals u of the different channels synthesized by the second synthesizer 32 may be acquired via conversion of the related input signals $x_1$ to $x_5$ of the different channels.

The second synthesizer 32, for instance, may combine all of the converted signals u of the different channels, without separate processing, to generate a synthesized signal z. Alternatively, the second synthesizer 32 may apply a prescribed weight to each channel to generate the converted signals $u_{1s}$ to $u_{5s}$ of the respective channels, to which the prescribed weight has been applied. The first synthesizer 31 may synthesize the converted signals $u_{1s}$ to $u_{5s}$ to generate the synthesized signal z. In this case, the prescribed weight may be a converted-signal weight $\beta$.

The first synthesizer 31 may receive the at least one synthesized signal $u_{1s}$ to $u_{5s}$ from the second synthesizer 32. The first synthesizer 31 again synthesizes the at least one synthesized signal $u_{1s}$ to $u_{5s}$ to generate a synthesized signal z. More specifically, the first synthesizer 31 may synthesize the at least one synthesized signal $u_{1s}$ to $u_{5s}$, in a similar manner as exemplarily shown in FIG. 4 or FIG. 8, to generate the synthesized signal z.

Figure 12:
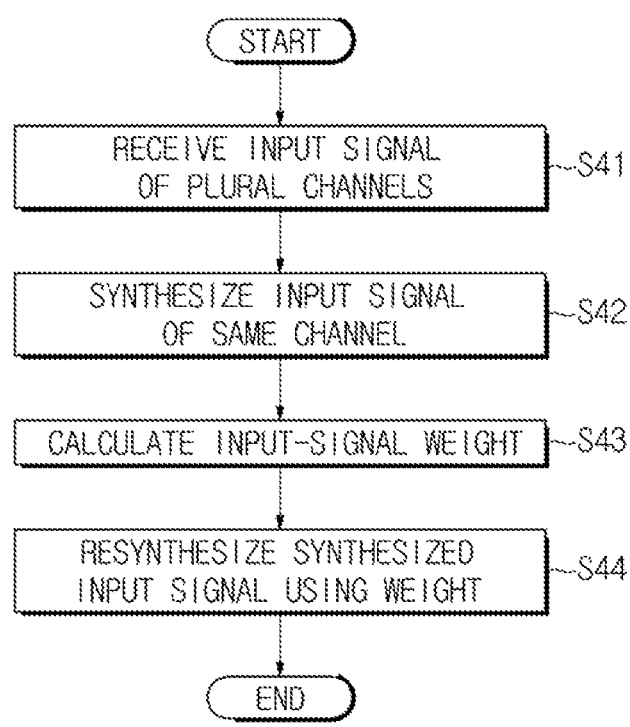
FIG. 12 is a flowchart of an image processing method according to an embodiment.

Hereinafter, an embodiment of an image processing method that may be implemented by the above-described image processing module 1 will be described. FIG. 12 is a flowchart showing an image processing method according to an embodiment.

As exemplarily shown in FIG. 12, according to an embodiment of the image processing method, input signals of plural channels may be input (S41). In this case, plural input signals x may be input through each channel. Thus, the number of input signals x may be calculated by multiplying the number of channels by the number of times a signal is input through each channel.

When the plural input signals x are input through each channel, the plural input signals x are synthesized on a per channel basis. In other words, as exemplarily shown in FIG. 4, plural input signals $x_{11}$ to $x_{13}$ of the same channel are synthesized (S42). Accordingly, as shown in FIG. 7, synthesized input signals $x_{1s}$ to $x_{4s}$ of plural channels, i.e., four channels, may be output. Here, the number of channels related to the synthesized input signals $x_{1s}$ to $x_{4s}$ may be equal to the number of channels through which the signals are input.

At least one input-signal weight $\omega$ to be applied to the synthesized input signals (e.g., $x_{1s}$ to $x_{4s}$) is calculated (S43). The input-signal weight $\omega$ may be acquired based on the input signals x, or may be acquired based on the synthesized input signals $x_{1s}$ to $x_{4s}$. In addition, the input-signal weight $\omega$ may be determined regardless of the input signals w or the synthesized input signals $x_{1s}$ to $x_{4s}$. The calculated input-signal weight $\omega$ may be different between the respective channels, may be equal between only a portion of the channels, or may be equal throughout the channels.

Figure 13:
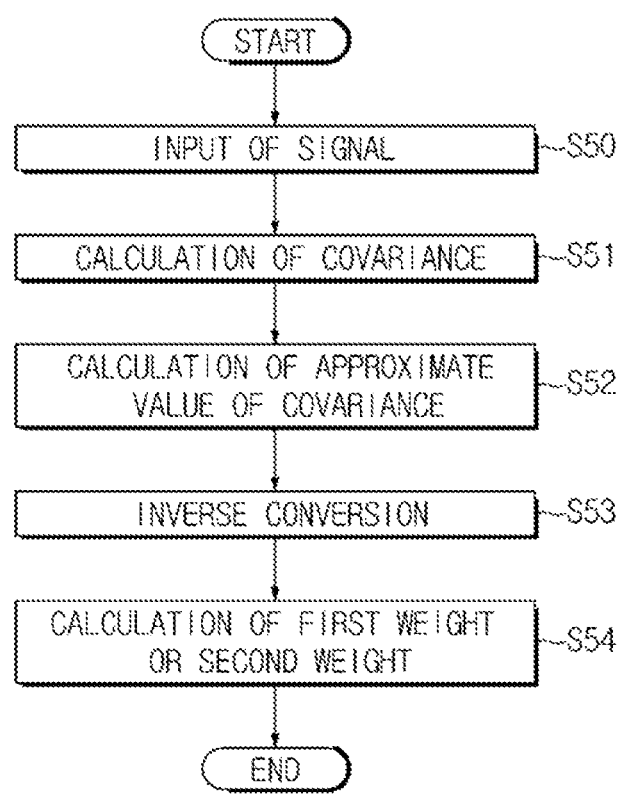
FIG. 13 is a flowchart of a weight calculation method according to an embodiment.

According to an embodiment, after a converted-signal weight $\beta$ is first calculated, the input-signal weight $\omega$ may be calculated using the converted-signal weight $\beta$. In this case, the input-signal weight $\omega$ may be calculated using the above-described Equation 11. FIG. 13 is a flowchart showing a weight calculation method according to an embodiment. According to the weight calculation method exemplarily shown in FIG. 13, when input signals x are input (S50), prescribed covariance $R_1$ with respect to the input signals x may be calculated (S51), and an approximate value of the prescribed covariance $R_1$, e.g., a Toeplitz matrix may be calculated (S52). Then, an inverse of the calculated approximate value, e.g., an inverse-matrix of the Toeplitz matrix is calculated (S53). Subsequently, a converted-signal weight $\beta$ or an input-signal weight $\omega$ is calculated using the calculated inverse of the approximate value, e.g., the inverse matrix of the Toeplitz matrix (S54). According to an embodiment, the converted-signal weight $\beta$ may first be calculated using the calculated inverse of the approximate value. Subsequently, the input-signal weight $\omega$ may be calculated using the calculated converted-signal weight $\beta$ and the prescribed conversion function V.

Next, as exemplarily shown in FIG. 12, the synthesized input signals $x_{1s}$ to $x_{4s}$ of the plural channels are again synthesized to acquire at least one synthesized signal z (S44). For instance, the synthesized input signals $x_{1s}$ to $x_{4s}$ of the plural channels are synthesized as exemplarily shown in FIG. 7. Here, the input signals $x_{1s}$ to $x_{4s}$ of the plural channels may be synthesized using the input-signal weight $\omega$ to generate the synthesized signal z. According to an embodiment, the synthesized signal z may be calculated by multiplying the input-signal weight $\omega$ by the synthesized input signals $x_{1s}$ to $x_{4s}$.

Figure 14:
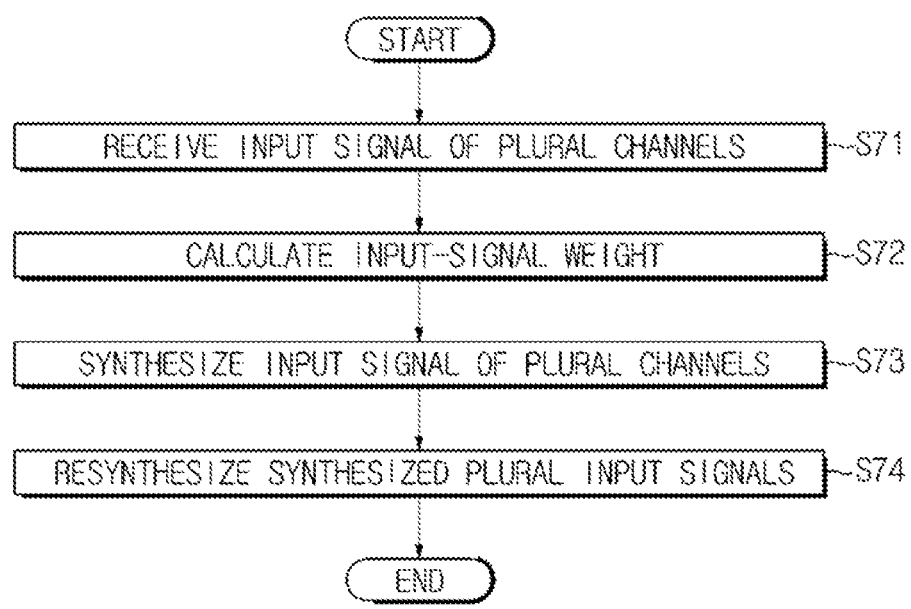
FIGS. 14 to 16 are flowcharts of an image processing method according to other embodiments.
Figure 15:
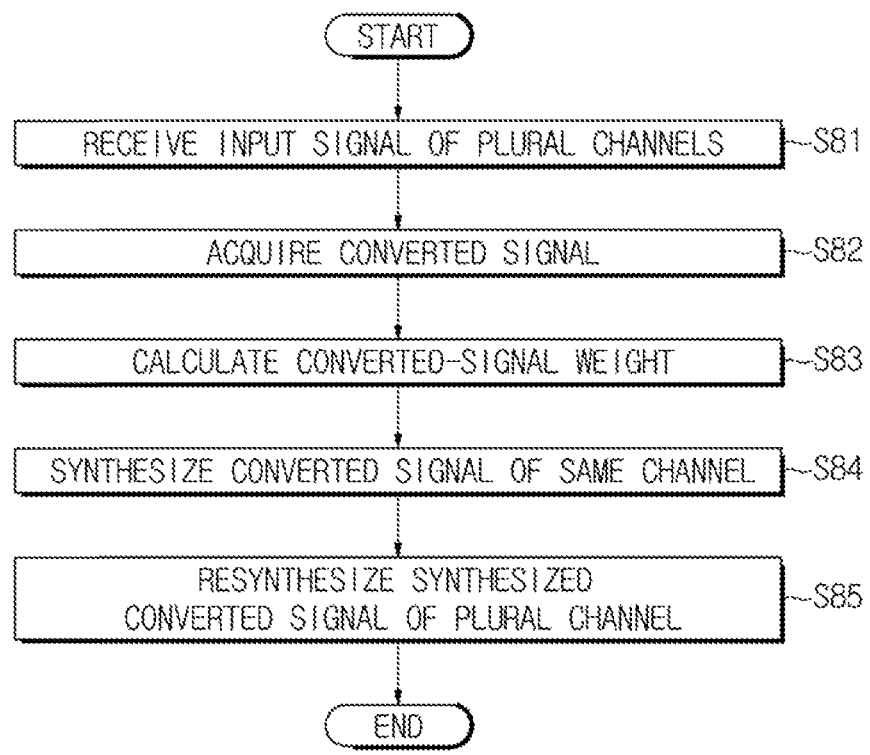
Figure 16:
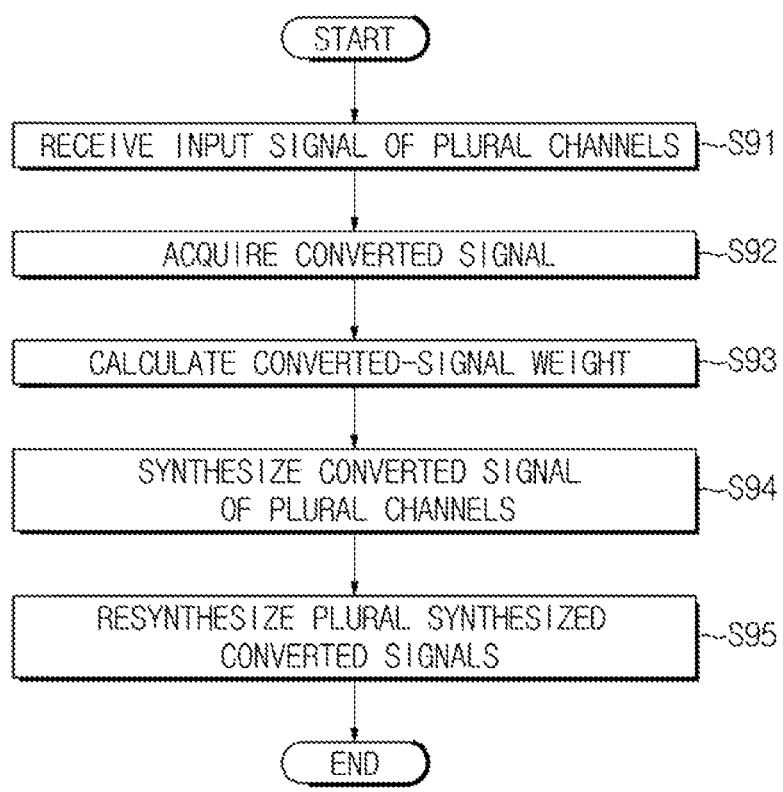

FIGS. 14 to 16 are flowcharts showing an image processing method according to other embodiments.

As exemplarily shown in FIG. 14, according to another embodiment of the image processing method, input signals x of plural channels are input (S71). In a similar manner as in the above-description, plural input signals x may be input through each channel.

At least one input-signal weight wt to be used for synthesis of the input signals x of the respective channels is calculated (S72). According to an embodiment, the input-signal weight $\omega$ may be determined according to Equation 11. The calculated input-signal weight $\omega$ may be substantially equal to the input-signal weight $\omega$ as described above with reference to FIG. 12.

The input signals x of the plural channels are synthesized (S73). More specifically, among the input signals of the different channels, input signals $x_{11}$ to $x_{41}$ of the respective channels, which may be related to each other or may correspond to each other in terms of an input time or input sequence, may be synthesized as exemplarily shown in FIG. 5.

In this case, the input signals x of the plural channels may be synthesized using the input-signal weight $\omega$ calculated in step S72. For instance, as exemplarily shown in Equation. 12, the above-described synthesis may be implemented via multiplication of the input-signal weight $\omega$ by the input signals x of the respective channels.

Once the input signals x of the respective channels are synthesized, the plural synthesized input signals (e.g., $x_{s1}$ to $x_{s3}$ in FIG. 9) are again synthesized (S74). More specifically, as exemplarily shown in FIG. 9, the plural synthesized input signals (e.g., $x_{s1}$ to $x_{s3}$) are synthesized to generate at least one synthesized signal z.

As exemplarily shown in FIG. 15, according to another embodiment of the image processing method, first, the input signals x of the plural channels are input (S81). In a similar manner as in the above-description, the plural input signals x may be input through each channel.

Converted signals u of the input signals x of the plural channels are acquired (S82). In this case, the converted signals u may be acquired by applying a prescribed conversion function V to the input signals x as represented in Equation 1.

The converted signals u, according to an embodiment, may be acquired by converting all of the plural input signals x, e.g., $x_{11}$ to $x_{43}$ in FIG. 7 input through the plural channels, or may be acquired by converting some of the plural input signals $x_{11}$ to $x_{43}$ input through the plural channels.

According to an embodiment, the converted signal u may be converted from a synthesized input signal ($x_{s1}$ of FIG. 5) that is acquired by synthesizing the plural corresponding input signals $x_{11}$ to $x_{41}$ of the different channels among the input signals x of the plural channels. Alternatively, the converted signal u may be converted from a synthesized input signal ($x_{1s}$ of FIG. 4) of the plural channels that is acquired by synthesizing the plural input signals $x_{11}$ to $x_{13}$ of the same channel.

A converted-signal weight β is calculated (S83). The converted-signal weight β may be calculated using the input signals x or the converted signals u. More specifically, to calculate the converted-signal weight β as exemplarily shown in FIG. 13, covariance $R_1$ with respect to the converted signals u may be calculated (S51, see Equation 5). Subsequently, an approximate value of the calculated covariance $R_1$ with respect to the converted signals u, e.g., a Toeplitz matrix approximate to the covariance $R_1$ may be calculated (S52, see FIG. 8), and an inverse of the calculated approximate value, e.g., an inverse-matrix of the Toeplitz matrix may be calculated (S53). Then, the converted-signal weight β may be calculated using the inverse of the calculated approximate value, e.g., the inverse-matrix of the Toeplitz matrix (S54, see Equation 9).

Subsequently, as exemplarily shown in FIG. 15, the plural converted signals u of the same channel are synthesized. In this case, as exemplarily shown in FIG. 5, the plural converted signals u may be synthesized. As a result, the synthesized converted signals of the plural channels are acquired (S84). Acquisition of the plural converted signals u of the same channel may be implemented before, after, or at the same time as calculation (S83) of the converted-signal weight β. When the converted signals u are converted from the synthesized input signals $x_{1s}$ that are acquired by synthesizing the input signals $x_{11}$ to $x_{13}$ of the same channel in the above-described step S82, step S84 may be omitted.

The synthesized converted signals of the plural channels are again synthesized as exemplarily shown in FIG. 7 (S85). In this case, the synthesized converted signals of the plural channels may be synthesized by applying the converted-signal weight β calculated in step S83 to each channel.

As exemplarily shown in FIG. 16, according to a further embodiment of the image processing method, input signals x of plural channels may be input. The plural input signals x may be input through each channel (S91).

Converted signals u of the input signals x of the plural channels are acquired (S92). In this case, the converted signals u corresponding to the input signals x may be acquired using a prescribed conversion function V.

The converted signals u, according to embodiments, may be converted from plural input signals x, e.g., $x_{11}$ to $x_{43}$ of plural channels in FIG. 7, or may be converted from synthesized input signals ($x_{s1}$ of FIG. 5) that are acquired by synthesizing corresponding input signals $x_{11}$ to $x_{41}$ of the plural channels. Alternatively, the converted signals u may be converted from synthesized input signals $x_{1s}$ of plural channels that are acquired by synthesizing plural input signals, e.g., $x_{11}$ to $x_{13}$ of the same channel in FIG. 4.

Subsequently, the converted-signal weight β is calculated (S93). The converted-signal weight β may be calculated using the input signals x or the converted signals u. To this end, a weight calculation method as exemplarily shown in FIG. 13 may be used. More specifically, the above-described Equation 5, Equation 6, Equation 8, and Equation 9 may be used.

The converted signals u of the plural channels are synthesized (S94). In this case, the converted signals u of each channel may be synthesized as exemplarily shown in FIG. According to an embodiment, the converted signals u of the plural channels may be synthesized by applying the converted-signal weight β calculated in step S93 to each channel, to generate plural synthesized converted signals.

The plural synthesized converted signals are again synthesized (S94). More specifically, the plural synthesized converted signals may again be synthesized as exemplarily shown in FIG. 7. As a result, a synthesized signal z is generated.

The image processing module 1 and the image processing method as described above may be used, for example, in ultrasound imaging apparatuses, sound navigation and ranging (SONAR) apparatuses, or radars. The image processing module 1 and the image processing method may also be used in array microphones or array speakers in the field of sound signal processing. In addition, the image processing module 1 and the image processing method may also be used in array antennas.

Hereinafter, an embodiment of an ultrasound imaging apparatus, to which the image processing module 1 as described above is applied, will be described by way of example with reference to FIGS. 17 to 24, and a control method of the ultrasound imaging apparatus will be described.

Figure 17:
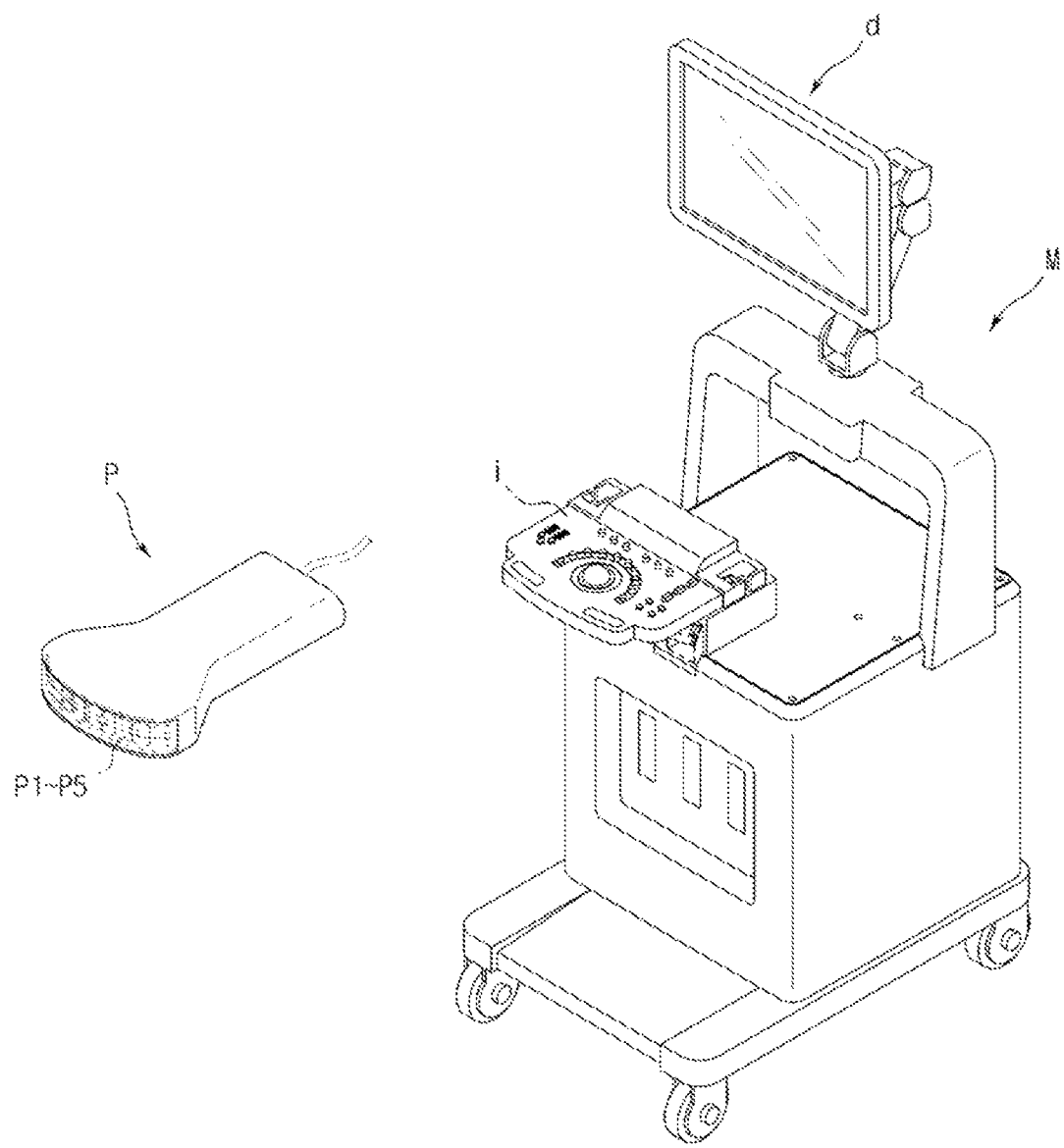
FIG. 17 is a perspective view of an ultrasound imaging apparatus according to an embodiment.
Figure 18:
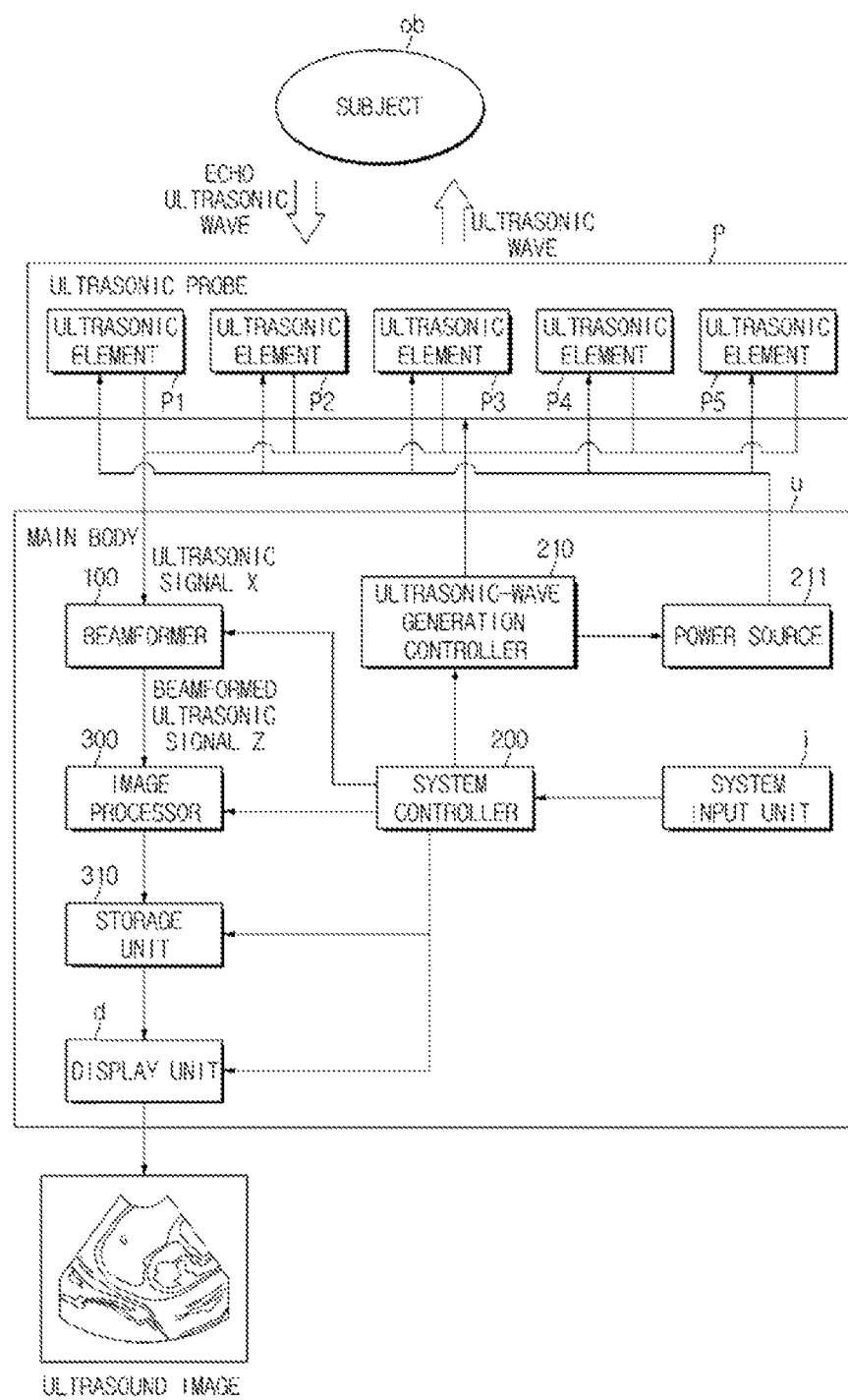
FIG. 18 is a view showing a configuration of an ultrasound imaging apparatus according to an embodiment.

FIG. 17 is a perspective view showing an ultrasound imaging apparatus according to an embodiment, and FIG. 18 is a view showing a configuration of an ultrasound imaging apparatus according to an embodiment.

The ultrasound imaging apparatus collects ultrasonic waves transmitted from a target region inside a subject, and generates an ultrasound image based on the collected ultrasound information. To this end, the ultrasound imaging apparatus, as exemplarily shown in FIGS. 17 and 18, may include an ultrasonic probe P configured to receive ultrasonic waves from a subject ob and convert the ultrasonic waves into electrical signals, i.e. ultrasonic signals, and a main body M configured to generate an ultrasound image based on the ultrasonic signals.

The ultrasonic probe P collects information regarding a target region of the subject ob using ultrasonic waves. The ultrasonic probe P may be, for example, an ultrasonic probe as exemplarily shown in FIG. 18.

More specifically, referring to FIGS. 17 and 18, the ultrasonic probe P may include a plurality of ultrasonic elements P1 to P5.

According to an embodiment, the plurality of ultrasonic elements P1 to P5 may generate ultrasonic waves having a predetermined frequency to emit the ultrasonic waves to the target region inside the subject ob. More specifically, the plurality of ultrasonic elements P1 to P5 may generate ultrasonic waves according to a pulse signal or alternating current applied to the plurality of ultrasonic elements P1 to P5 under control of an ultrasonic-wave generation controller 210 that is provided in the main body M. Ultrasonic waves generated by the plurality of ultrasonic elements P1 to P5 may be emitted to the target region inside the subject ob. In this case, the plurality of ultrasonic elements P1 to P5 may focus the ultrasonic waves on a particular target region inside the subject ob.

The plurality of ultrasonic elements P1 to P5 of the ultrasonic probe P may receive ultrasonic waves generated from an external source. The plurality of ultrasonic elements P1 to P5 may vibrate according to a frequency of the received ultrasonic waves to output alternating current corresponding to the frequency of the received ultrasonic waves. In other words, the plurality of ultrasonic elements P1 to P5 may convert the received ultrasonic waves into prescribed electrical signals x (hereinafter, referred to as ultrasonic signals). In this case, the output ultrasonic signals x may be analog signals. As described above, when the plurality of ultrasonic elements P1 to P5 emit ultrasonic waves to the target region inside the subject ob, the plurality of ultrasonic elements P1 to P5 may receive the ultrasonic waves reflected from the target region inside the subject, i.e. echo ultrasonic waves.

According to an embodiment, all of the ultrasonic elements P1 to P5 of the ultrasonic probe P may emit ultrasonic waves to the target region inside the subject ob and receive echo ultrasonic waves reflected from the target region. According to another embodiment, some of the plural ultrasonic elements P1 to P5 may be used to emit ultrasonic waves to the target region inside the subject ob, and some other ultrasonic elements may be used to receive the ultrasonic waves reflected from the target region.

Figure 19:
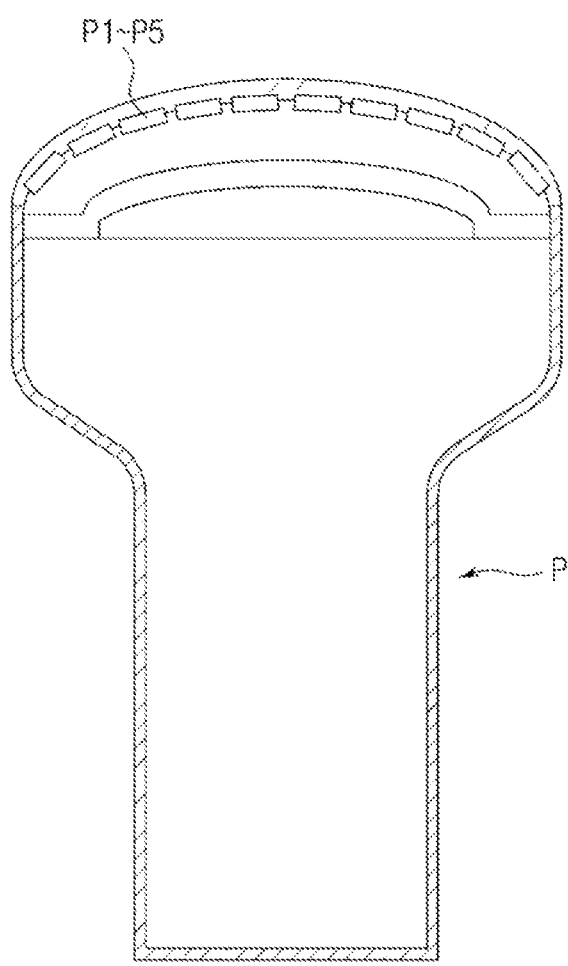
FIG. 19 is a plan view of an ultrasonic probe according to an embodiment.

FIG. 19 is a plan view showing an ultrasonic probe according to an embodiment. As exemplarily shown in FIGS. 17 and 19, the plural ultrasonic elements P1 to P5 may be installed at an end portion of the ultrasonic probe P. For instance, 64 or 128 ultrasonic elements P1 to P5 may be installed at the end portion of the ultrasonic probe P. The respective ultrasonic elements P1 to P5 installed at the end portion of the ultrasonic probe P may convert the received ultrasonic waves into ultrasonic signals X to output the ultrasonic signals X. As a result, as exemplarily shown in FIG. 19, ultrasonic signals may be transmitted to the main body M through plural channels X1 to X10 equal in number to the number of the ultrasonic elements P1 to P5, e.g., 64 to 128 channels.

According to an embodiment, the plurality of ultrasonic elements P1 to P5 may serve as an ultrasonic transducer disposed at the end portion of the ultrasonic probe P.

A transducer is a device that converts prescribed energy, e.g., mechanical wave energy or luminous energy into a different form of energy, e.g., luminous energy or mechanical wave energy. The ultrasonic transducer implements conversion between mechanical wave energy and electric energy. More specifically, the ultrasonic transducer may vibrate according to a prescribed input pulse current to generate ultrasonic waves, or may vibrate according to ultrasonic waves transmitted from an external source, e.g., echo ultrasonic waves to generate electrical signals having a prescribed frequency. As such, the ultrasonic transducer may implement all functions of an ultrasonic-wave generator and an ultrasonic-wave receiver.

More specifically, the ultrasonic transducer receives alternating current from a power source 211, e.g., an external power supply device or an internal storage device, such as a battery. As a piezoelectric vibrator or a thin film of the ultrasonic transducer vibrates according to power applied thereto, the ultrasonic transducer generates ultrasonic waves. On the other hand, when a piezoelectric material or a thin film vibrates according to ultrasonic waves applied thereto, the ultrasonic transducer generates alternating current having a frequency corresponding to a vibration frequency of the piezoelectric material or the thin film, thereby converting the ultrasonic waves into electrical signals, i.e. ultrasonic signals X.

The ultrasonic transducer may be a magnetostrictive ultrasonic transducer using magnetostrictive effects of a magnetic substance, a piezoelectric ultrasonic transducer using piezoelectric effects of a piezoelectric material, or a capacitive micromachined ultrasonic transducer (CMUT) to receive and transmit ultrasonic waves using vibration of hundreds to thousands of micromachined thin films. In addition, various other transducers that may generate ultrasonic waves according to electrical signals or may generate electrical signals according to ultrasonic waves may be used.

Figure 20:
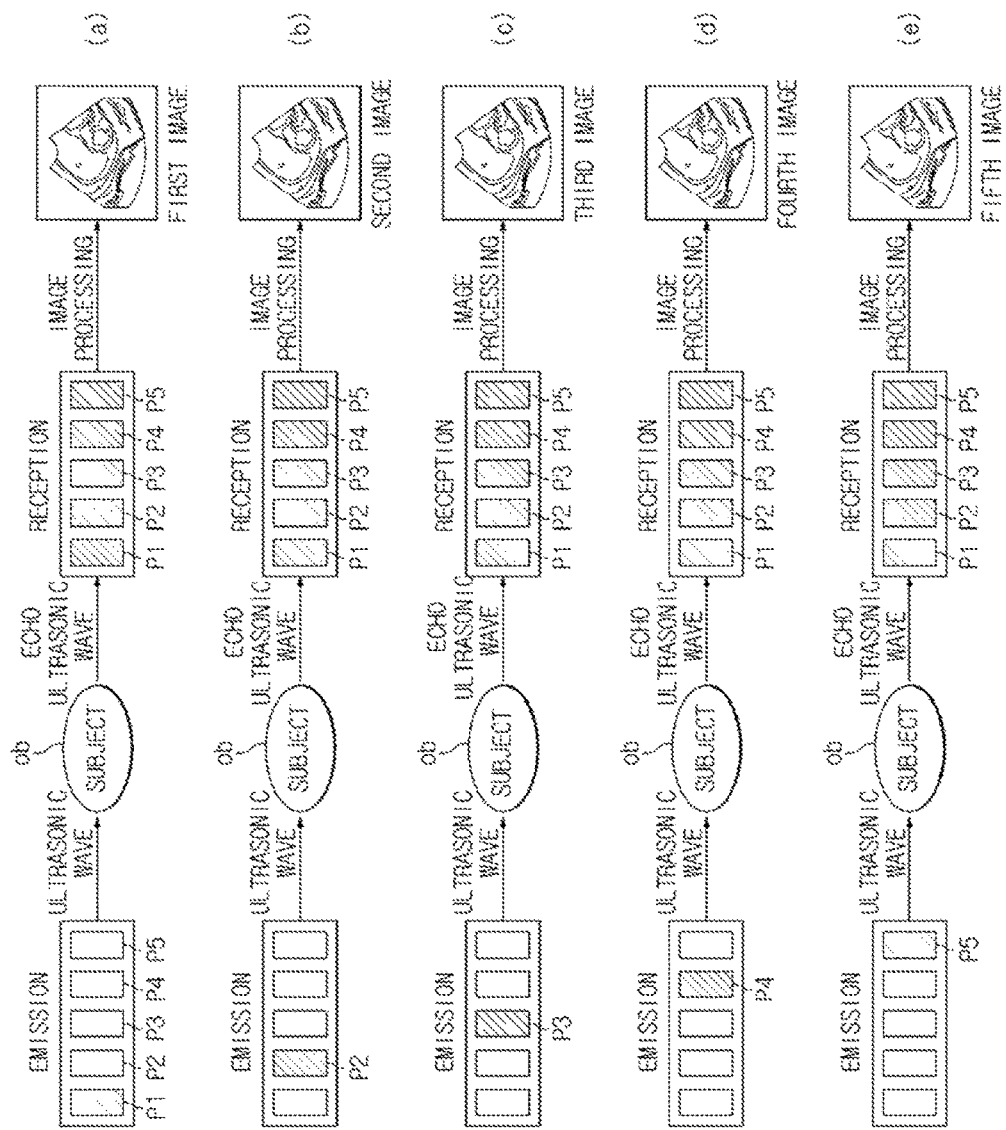
FIG. 20 is an explanatory view of an operation of ultrasonic elements of an ultrasonic probe according to an embodiment.

FIG. 20 is an explanatory view of an operation of the ultrasonic elements of an ultrasonic probe according to an embodiment.

According to an embodiment, when emitting ultrasonic waves, all of ultrasonic elements P1 to P5 may not need to simultaneously emit ultrasonic waves to the subject ob. For instance, the respective ultrasonic elements P1 to P5 may emit ultrasonic waves to different target regions or the same target region inside the subject ob at different times. In addition, respective ultrasonic element groups may emit ultrasonic waves to the same target region or different target regions inside the subject ob at different times. In this case, each ultrasonic element group refers to a group consisting of some of the plural ultrasonic elements P1 to P5.

In other words, only a prescribed single ultrasonic element, e.g., a first ultrasonic element P1 may emit ultrasonic waves to a target region at a prescribed ultrasonic-wave emission timing, or a prescribed ultrasonic element group, e.g., only a group of first and second ultrasonic elements P1 and P2 may emit ultrasonic waves to a target region at a prescribed ultrasonic-wave emission timing.

In this case, according to an embodiment, each of the ultrasonic elements P1 to P5 or a prescribed ultrasonic element group may sequentially emit ultrasonic waves to the same target region or different target regions according to a prescribed sequence. For instance, starting from an ultrasonic element proximate to a particular edge, the ultrasonic elements sequentially emit ultrasonic waves until an ultrasonic element proximate to the other edge emits ultrasonic waves, and these ultrasonic elements may emit ultrasonic waves to the same target region or different target regions inside the subject ob.

When ultrasonic waves emitted by a single ultrasonic element or some ultrasonic elements are reflected from the target region, the echo ultrasonic waves reflected from the target region may be received by plural ultrasonic elements P1 to P5. In this case, all of the plural ultrasonic elements P1 to P5 may receive echo ultrasonic waves reflected from the target region.

As a result, the ultrasonic probe P may allow individual ultrasonic elements or some ultrasonic elements among the plural ultrasonic elements P1 to P5 to emit ultrasonic waves to the subject ob at different times, thereby emitting ultrasonic waves to the subject ob plural times.

Hereinafter, a process in which a single ultrasonic element generates ultrasonic waves at different times and plural ultrasonic elements receive ultrasonic waves will be described in greater detail.

Referring to FIG. 20(a), for instance, first, only the first ultrasonic element P1 among the plural ultrasonic elements P1 to P5 is operated to emit ultrasonic waves to the subject ob. In this case, a pulse signal is only applied to the first ultrasonic element P1 and no pulse signal is applied to the other ultrasonic elements P2 to P5. Accordingly, only the first ultrasonic element P1 may generate ultrasonic waves.

The ultrasonic waves emitted by the first ultrasonic element P1 are reflected from the subject ob.

Echo ultrasonic waves reflected from the subject ob are transmitted to the plural ultrasonic elements P1 to P5. According to an embodiment, as exemplarily shown in FIG. 20(a), all of the plural ultrasonic elements P1 to P5 may receive the echo ultrasonic waves reflected from the subject ob, and convert the received echo ultrasonic waves into ultrasonic signals. According to another embodiment, some of the plural ultrasonic elements P1 to P5, e.g., only odd-numbered ultrasonic elements or even-numbered ultrasonic elements may convert the echo ultrasonic waves reflected from the subject ob to generate ultrasonic signals. The ultrasonic signals generated by the plural ultrasonic elements P1 to P5 may be stored in a prescribed storage space (not shown) of the ultrasonic probe P, or may be transmitted to the main body M to be stored in the main body M. The main body M may generate an ultrasound image, e.g., a first image based on the generated ultrasonic signals.

Next, referring to FIG. 20(b), the second ultrasonic element P2 may be operated to emit ultrasonic waves to the subject ob. Likewise, all or some of the plural ultrasonic elements P1 to P5 may receive echo ultrasonic waves reflected from the subject ob to convert the echo ultrasonic waves into ultrasonic signals. The converted ultrasonic signals may be used for generation of a second image. Similar to the above description, the ultrasonic signals collected via operation of the second ultrasonic element P2 may be transmitted to a beamformer 100 of the main body M.

Then, referring to FIGS. 20(c) to 20(e), the third to fifth ultrasonic elements P3 to P5 may be sequentially operated to emit ultrasonic waves to the subject ob. Likewise, all or some of the plural ultrasonic elements P1 to P5 may receive echo ultrasonic waves reflected from the subject ob to convert the echo ultrasonic waves into ultrasonic signals. Prescribed ultrasound images, e.g., third to fifth images may be generated using the converted ultrasonic signals. Likewise, the ultrasonic signals acquired via emission of ultrasonic waves from the third to fifth ultrasonic elements P3 to P5 may be transmitted to the beamformer 100 of the main body M.

In this way, as ultrasonic waves are emitted plural times and reflected from the subject ob plural times, ultrasonic signals of plural channels may be transmitted to the main body M plural time. In other words, each channel may transmit plural ultrasonic signals to the main body M. In this case, the number of ultrasonic signals transmitted to the main body M through each channel may be equal to the number of ultrasonic waves emitted to the subject ob by the individual ultrasonic elements P1 to P5 of the ultrasonic probe P.

In the case in which the individual ultrasonic elements P1 to P5 or individual ultrasonic element groups emit ultrasonic waves, all of the individual ultrasonic elements P1 to P5 or the individual ultrasonic element groups may have the same focal point Tx or different focal points Tx. Alternatively, some ultrasonic elements may have the same focal point Tx, and some other ultrasonic elements may have different focal points Tx.

In this case, the ultrasonic probe P may generate various forms of ultrasonic beams. In one example, as described above, the ultrasonic elements P1 to P5 may sequentially transmit ultrasonic waves to diffuse the ultrasonic waves over a wider region inside the subject ob. In another example, plural ultrasonic element groups, each including plural ultrasonic elements, may be sequentially operated to generate ultrasonic beams such that the ultrasonic beams are transmitted in a diffusive manner. In still another example, plural ultrasonic element groups, each including plural ultrasonic elements, may sequentially generate transmission beams such that the transmission beams are focused upon a particular point and then diffused. In a further example, plural ultrasonic elements of each ultrasonic element group may generate plane waves.

As exemplarily shown in FIG. 18, according to an embodiment, the main body M may include the beamformer 100, a system controller 200, the ultrasonic-wave generation controller 210, an image processor 300, a storage unit 310, an input unit i, and a display unit d.

The beamformer 100 receives ultrasonic signals x of plural channels from the ultrasonic probe P, and beamforms the ultrasonic signals x.

Figure 21:
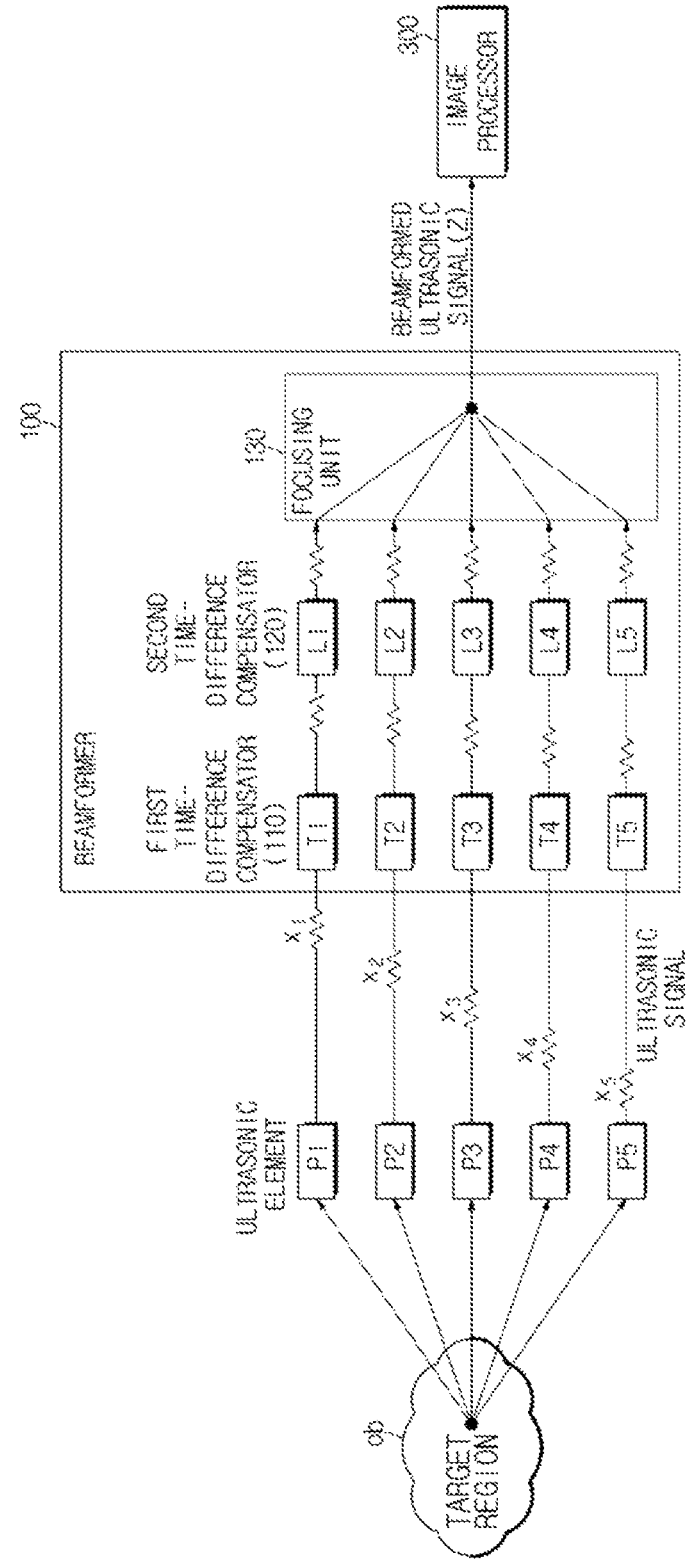
FIG. 21 is a view showing a configuration of a beamformer of an ultrasound imaging apparatus according to an embodiment.

FIG. 21 is a view showing a beamformer according to an embodiment according to an embodiment.

As exemplarily shown in FIG. 21, the beamformer 100 may include a first time-difference compensator 110, a second time-difference compensator 120, and a focusing unit 130.

Ultrasonic waves generated or reflected from the target region of the subject ob are received by the ultrasonic elements P1 to P5 as described above with reference to FIG. 18.

Distances between the respective ultrasonic elements P1 to P5 installed to the ultrasonic probe P and the target region are different while the velocity of sound may be substantially constant within the same medium. Therefore, as exemplarily shown in FIG. 20, when the respective ultrasonic elements P1 to P5 generate ultrasonic waves at the same times and collect the ultrasonic waves, the ultrasonic waves generated by the respective ultrasonic elements P1 to P5 may reach the target region of the subject ob at different times. Likewise, even in the case of ultrasonic waves reflected from the same target region at the same time, the respective ultrasonic elements P1 to P5 may receive the ultrasonic waves reflected from the same target region at different times because of a distance difference between the respective ultrasonic elements P1 to P5 and the target region.

In other words, the individual ultrasonic elements P1 to P5 receive echo ultrasonic waves generated by the ultrasonic waves that have been emitted at the same time and reflected from the same target region at different times. As a result, ultrasonic signals output from the respective ultrasonic elements P1 to P5 may have a prescribed time difference. Accordingly, even when the respective ultrasonic elements P1 to P5 receive ultrasonic waves at different times, the ultrasonic waves may be ultrasonic waves reflected from the same target region at the same time. Therefore, it may be desirable to compensate for a time difference between ultrasonic signals generated by the respective ultrasonic elements P1 to P5.

The first time-difference compensator 110 and the second time-difference compensator 120 of the beamformer 100 serve to compensate for the above-described time difference between the ultrasonic signals. For instance, the first time-difference compensator 110 and the second time-difference compensator 120, as exemplarily shown in FIG. 21, may delay transmission of ultrasonic signals x input through a particular channel by a predetermined degree to compensate for a time difference between the ultrasonic signals $x_1$ to $x_5$ input through the respective channels. As a result, the ultrasonic signals $x_1$ to $x_5$ of the respective channels may reach the focusing unit 130 at the same time.

Here, the first time-difference compensator 110 may compensate for a time difference between ultrasonic waves arriving at the target object ob using time taken for ultrasonic waves generated by the individual ultrasonic elements P1 to P5 to reach the target region. That is, the first time-difference compensator 110 implements focusing delay to achieve focusing in consideration of time taken for a sound field generated by the individual ultrasonic elements P1 to P5 to reach a desired focal point.

The second time-difference compensator 120 compensates for a time difference between ultrasonic waves arriving at the ultrasonic elements P1 to P5 in consideration of time taken for echo ultrasonic waves reflected from the target region to reach the individual ultrasonic elements P1 to P5.

According to an embodiment, as exemplarily shown in FIG. 21, first, the first time-difference compensator 110 may compensate for a time difference caused upon reception of ultrasonic waves at the target object ob, and subsequently the second time-difference compensator 120 may compensate for a time difference caused upon reception of ultrasonic waves at the ultrasonic elements P1 to P5 by delaying ultrasonic signals compensated by the first time-difference compensator 110. According to another embodiment, first, the second time-difference compensator 120 may compensate for a time difference caused upon reception of the ultrasonic waves at the ultrasonic elements P1 to P5, and subsequently the first time-difference compensator 110 may compensate for a time difference caused upon reception of the ultrasonic waves at the target object ob.

The focusing unit 130 focuses ultrasonic signals x', a time difference of which has been compensated for.

The focusing unit 130 combines ultrasonic signals $x_1$ to $x_5$ of plural channels to output beamformed ultrasonic signals, thereby generating at least one ultrasound image based on echo ultrasonic waves.

According to an embodiment, the focusing unit 130 applies a prescribed weight, i.e. a beamforming coefficient to each input ultrasonic signal to accentuate or relatively attenuate a signal of a particular channel for focusing the ultrasonic signal. As such, generation of an ultrasound image depending on user requirements or with improved user convenience may be accomplished. In this case, the focusing unit 130 may implement focusing of ultrasonic signals using a beamforming coefficient that is determined regardless of ultrasonic signals output by the ultrasonic receiver P12 (data-independent beamforming). In addition, the focusing unit 130 may calculate an appropriate (e.g., optimum) beamforming coefficient based on input ultrasonic signals, and implement focusing of ultrasonic signals using the calculated beamforming coefficient (data-dependent beamforming).

Hereinafter, an embodiment of the focusing unit 130 of the beamformer 100 will be described with reference to FIGS. 22 and 23.

Figure 22:
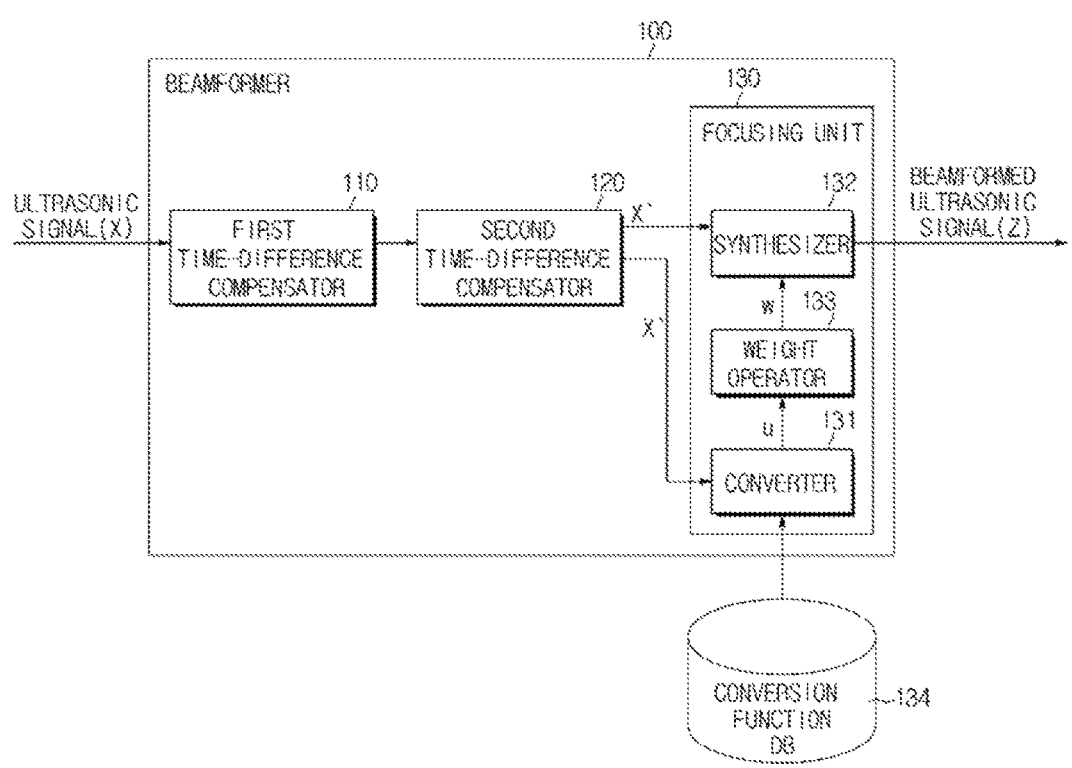
FIGS. 22 and 23 are views showing configurations of beamformers according to other embodiments.

FIG. 22 is a view showing a configuration of a beamformer according to another embodiment. As exemplarily shown in FIG. 22, the focusing unit 130 may include a converter 131, a synthesizer 132, and a weight operator 133.

The converter 131 receives plural ultrasonic signals x' of plural channels, a time difference of which has been compensated for by the first time-difference compensator 110 and the second time-difference compensator 120, and converts the plural input ultrasonic signals x' to generate converted ultrasonic signals u. According to an embodiment, the converter 131 may transmit the generated converted ultrasonic signals u to the weight operator 133 as exemplarily shown in FIG. 22.

The converter 131 may generate the converted ultrasonic signals u using a prescribed conversion function V. In this case, the converter 131 may calculate the converted ultrasonic signals u using the above-described Equation 1.

The converter 131 may call the prescribed conversion function V from a conversion function database 134, and generate the converted ultrasonic signals u using the called conversion function V. In this case, the converter 131 may select an appropriate conversion function V from the conversion function database 134, and generate the converted ultrasonic signals u of the ultrasonic signals x' based on the selected conversion function V.

According to an embodiment, the conversion function database 134 may store at least one conversion function V. In this case, the at least one conversion function V stored in the conversion function database 134 may be previously calculated based on various forms of ultrasonic signals that may be experimentally or theoretically acquired. For instance, the at least one conversion function V stored in the conversion function database 134 may be calculated using several ultrasonic signals acquired by emitting ultrasonic waves to a separate specimen.

In addition, conversion functions V stored in the conversion function database 134 may include a single basis vector or a combination of plural basis vectors acquired based on a previously calculated beamforming coefficient. The beamforming coefficient may be calculated using various forms of ultrasonic signals x that may be experimentally or theoretically acquired. In this case, the beamforming coefficient may be, for example, an optimum beamforming coefficient acquired using minimum distribution of ultrasonic signals of plural channels. Basis vectors based on the beamforming coefficient may be acquired via main component analysis of the beamforming coefficient. Plural basis vectors of the conversion function V may be substantially perpendicular to one another, and may be eigenvectors or Fourier basis vectors.

According to another embodiment, the conversion function database 134 may store at least one basis vector for the conversion function V. In this case, the converter 131 may call the at least one basis vector from the conversion function database 134, and generate the conversion function V suitable for ultrasonic signals using the called at least one basis vector.

The weight operator 133, according to an embodiment, receives the converted ultrasonic signals u from the converter 131 as exemplarily shown in FIG. 22, and calculates at least one weight to be used by the synthesizer 132 based on the converted ultrasonic signals u. Although not shown in the drawing, the weight operator 133 may directly receive ultrasonic signals x', a time difference of which has been compensated for, from the second time-difference compensator 120, and calculate at least one weight based on the received ultrasonic signals x'.

According to an embodiment, the weight, calculated by the weight operator 133, may be an ultrasonic signal weight ω to be applied to the ultrasonic signals x' transmitted from the second time-difference compensator 120.

The weight operator 133 may calculate covariance with respect to the converted signals u transmitted from the converter 131. In this case, the above-described Equation 5 may be used. According to an embodiment, the weight operator 133 may directly receive ultrasonic signals x, a time difference of which has been compensated for, from the second time-difference compensator 120, and calculate covariance $R_1$ using a prescribed conversion function V read out from the conversion function database 134. In this case, the above-described Equation 6 may be used.

Next, the weight operator 133 calculates an approximate value of the covariance $R_1$ based on the calculated covariance $R_1$. In this case, the approximate value of the covariance $R_1$ may be expressed as an approximate matrix, and the approximation matrix may be a Toeplitz matrix. More specifically, the weight operator 133 may generate an approximate matrix in the form of a Toeplitz matrix based on the covariance $R_1$ expressed in matrix form according to the above-described Equation 8. Since a Toeplitz matrix simplifies calculation of an inverse-matrix as described above, calculation of an inverse matrix may be faster while using less computational resources.

The weight operator 133 calculates an approximate value, e.g., an inverse-matrix of a Toeplitz matrix, and calculates a converted ultrasonic signal weight $\beta$ using the calculated inverse-matrix. In this case, the above-described Equation 9 may be used. The converted ultrasonic signal weight $\beta$ may be used as a beamforming coefficient when the synthesizer 132 synthesizes the converted signals u to generate a beamformed ultrasonic signal z.

Next, the weight operator 133 may calculate an ultrasonic signal weight $\omega$ based on the converted ultrasonic signal weight $\beta$. In this case, the weight operator 133 may calculate the ultrasonic signal weight $\omega$ using the above-described Equation 11. In other words, the weight operator 133 may multiply the converted ultrasonic signal weight $\beta$ by the conversion function V to calculate and acquire the ultrasonic signal weight $\omega$. The weight operator 133 may read out a prescribed conversion function V from the conversion function database 134, and apply the readout conversion function V to the ultrasonic signal weight $\omega$. In this case, the conversion function V used to calculate the ultrasonic signal weight $\omega$ may be equal to or different from the conversion function V used to calculate the converted ultrasonic signals u. The ultrasonic signal weight $\omega$ acquired by the weight operator 133 may be used as a beamforming coefficient when the synthesizer 132 synthesizes ultrasonic signals x', a time difference of which has been compensated for, to generate the beamformed ultrasonic signal z.

A weight calculated by the weight operator 133, e.g., the ultrasonic signal weight $\omega$ may be transmitted to the synthesizer 132.

The synthesizer 132 may synthesize the ultrasonic signals x', a time difference of which has been compensated for, to generate the beamformed ultrasonic signal z. More specifically, the synthesizer 132 may synthesize ultrasonic signals as exemplarily shown in FIGS. 7 and 9.

For instance, as exemplarily shown in FIG. 7, plural ultrasonic signals of respective channels may first be synthesized to generate synthesized ultrasonic signals of the plural channels. Next, the synthesized ultrasonic signals of the plural channels may again be synthesized to generate the beamformed ultrasonic signal z. In the case of resynthesizing the synthesized ultrasonic signals of the plural channels, the synthesizer 132 may implement resynthesis of the synthesized ultrasonic signals of the plural channels using a prescribed weight. More specifically, the synthesizer 132 may generate the beamformed ultrasonic signal z by multiplying the synthesized ultrasonic signals of the plural channels by the prescribed weight. In this case, the prescribed weight may be the ultrasonic signal weight $\omega$ transmitted from the weight operator 133. In this case, Equation 12 may be used for calculation.

Alternatively, the synthesizer 132, as exemplarily shown in FIG. 9, may first synthesize ultrasonic signals of plural channels to generate plural synthesized ultrasonic signals. The synthesizer 132 may use at least one weight, e.g., an ultrasonic signal weight $\omega$ for synthesis of the ultrasonic signals of the plural channels. The plural synthesized ultrasonic signals may correspond respectively to plural ultrasound images, e.g., first to fifth images as exemplarily shown in FIG. 20. Next, the synthesizer 132 may again synthesize the plural synthesized ultrasonic signals to generate a beamformed ultrasonic signal z.

The beamformed ultrasonic signal z output from the synthesizer 132 may be transmitted to the image processor 300 as exemplarily shown in FIGS. 18 and 22.

Figure 23:
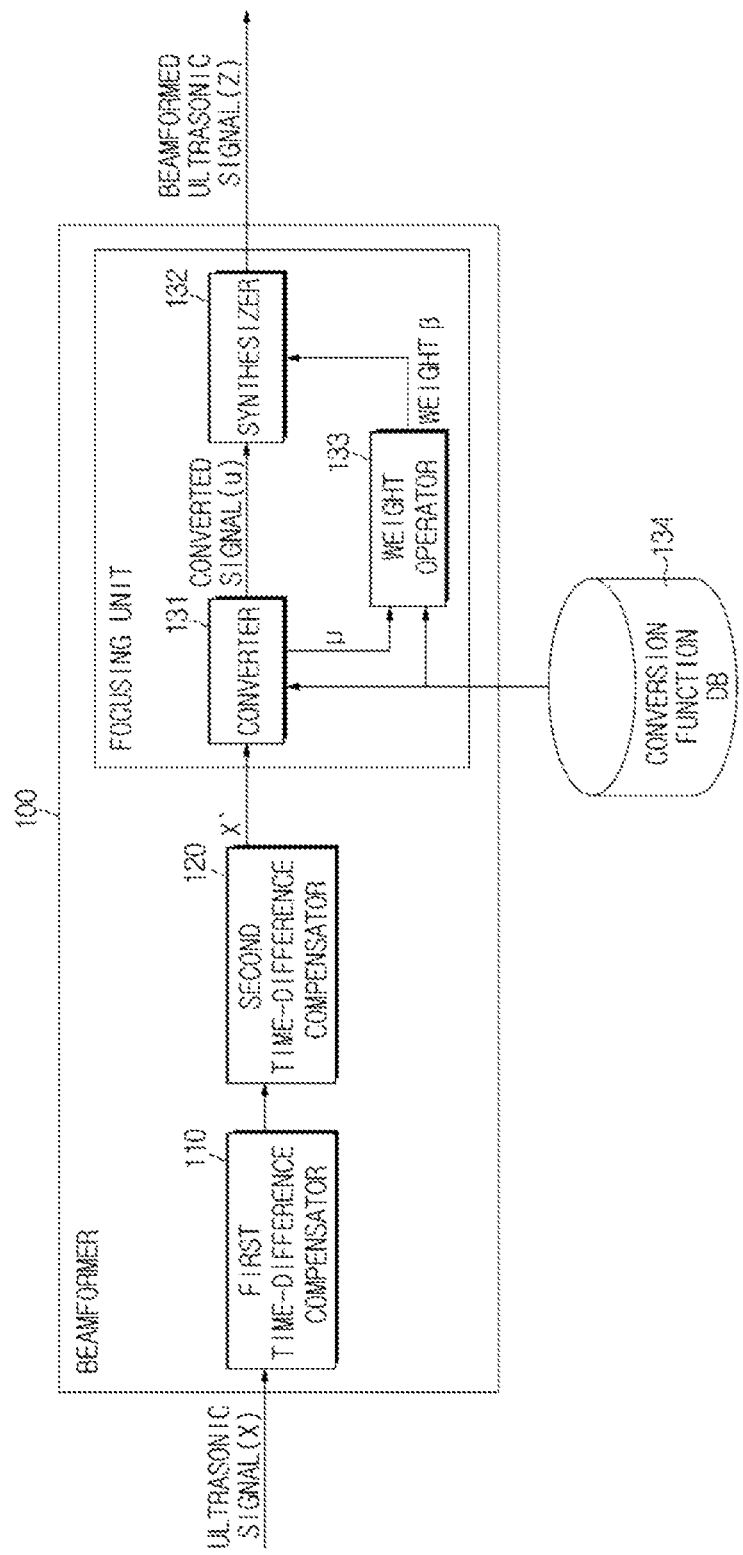

FIG. 23 is a view showing a configuration of a beamformer according to still another embodiment. Similar to FIG. 22, the focusing unit 130, as exemplarily shown in FIG. 23, may include the converter 131, the synthesizer 132, and the weight operator 133.

The converter 131 converts plural ultrasonic signals x' to generate converted ultrasonic signals u in a similar manner as in the above description. More specifically, the converter 131 may generate the converted ultrasonic signals u using a prescribed conversion function V. In addition, the converter 131 may call the prescribed conversion function V from the conversion function database 134, or generate the conversion function V based on at least one basis vector after calling the basis vector. The converter 131 may generate the converted ultrasonic signals u using the called or generated conversion function V. As exemplarily shown in FIG. 23, the converter 131 transmits the converted ultrasonic signals u to both the weight operator 133 and the synthesizer 132.

The weight operator 133, according to an embodiment, as exemplarily shown in FIG. 23, receives the converted ultrasonic signals u from the converter 131, and calculates at least one weight to be used by the synthesizer 132 based on the received converted ultrasonic signals u. Alternatively, the weight operator 133 may directly receive the ultrasonic signals x', a time difference of which has been compensated for, from the second time-difference compensator 120, and calculate at least one weight based on the received ultrasonic signals x'.

According to an embodiment, the weight operator 133 may calculate a converted ultrasonic signal weight $\beta$ for use in synthesis of the ultrasonic signals u converted by the converter 131.

More specifically, the weight operator 133 calculates covariance $R_1$ with respect to the converted signals u using Equation 5 or Equation 6 as described above, calculates an approximate value of the covariance $R_1$, and calculates an inverse-matrix of the approximate value. In this case, the approximate value of the covariance $R_1$ may be a Toeplitz matrix. In this case, the Toeplitz matrix may be calculated according to Equation 8. Then, a converted ultrasonic signal weight $\beta$ is calculated using the calculated inverse-matrix. In this case, the above-described Equation 9 may be used. The converted ultrasonic signal weight $\beta$ may be used as a beamforming coefficient when the synthesizer 132 synthesizes the converted signals u to generate a beamformed ultrasonic signal z.

The converted ultrasonic signal weight $\beta$ calculated by the weight operator 133 may be used as a beamforming coefficient when the synthesizer 132 synthesizes the converted ultrasonic signals u to generate the beamformed ultrasonic signal z.

A weight calculated by the weight calculator 133, e.g., the converted ultrasonic signal weight $\beta$ may be transmitted to the synthesizer 132.

The synthesizer 132 may synthesize the converted ultrasonic signals u to generate a beamformed ultrasonic signal z. In a similar manner as in the above description, the synthesizer 132 may synthesize the converted ultrasonic signals u as exemplarily shown in FIGS. 7 and 9.

For instance, as exemplarily shown in FIG. 7, plural converted ultrasonic signals u of respective channels may be synthesized to generate synthesized converted ultrasonic signals of plural channels. Then, resynthesis of the synthesized converted ultrasonic signals of the plural channels may be implemented to generate a final beamformed ultrasonic signal z. In the case of resynthesizing the synthesized converted ultrasonic signals of the plural channels, the synthesizer 132 may use a prescribed weight, e.g., the converted ultrasonic signal weight β. In this case, Equation 13 may be used.

The synthesizer 132, as exemplarily shown in FIG. 9, may first synthesize converted ultrasonic signals of plural channels to generate plural synthesized converted ultrasonic signals, and again synthesize the plural synthesized converted ultrasonic signals to generate a beamformed ultrasonic signal z. In this case, the converted ultrasonic signal weight β transmitted from the weight operator 133 may be used for synthesis of the converted ultrasonic signals of the plural channels.

The beamformed ultrasonic signal z output from the synthesizer 132 may be transmitted to the image processor 220 as exemplarily shown in FIGS. 18 and 23.

Hereinafter, a beamforming process performed by the beamformer 100 will be described. The beamforming process performed by an ultrasound imaging apparatus may generally be represented by the following Equation 15.

$$z[n] = \sum_{m=0}^{M-1} w_m[n] x_m[n - \Delta_m[n]] \quad \text{Equation 15}$$

Here, n is a distance identification value, and $x_m$ is an ultrasonic signal of an $m^{th}$ channel. $\omega_m[n]$ is a beamforming coefficient ω with respect to the ultrasonic signal of the $m^{th}$ channel. $\Delta_m$ is a time delay value for delay of a transmission time of an ultrasonic signal input through a particular channel. $x_m[n-\Delta_m]$ is an ultrasonic signal of each channel, a time difference of which has been compensated for.

When a time difference of an input signal has been compensated for, z[n] may be represented by the following Equation 16.

$$z[n] = \sum_{m=0}^{M-1} w_m[n] y_m[n] \quad \text{Equation 16}$$

When the respective ultrasonic elements P1 to P5 or ultrasonic element groups generate ultrasonic waves at different times to transmit plural ultrasonic signals of plural channels to the beamformer 100 as described above, the beamforming process performed by the beamformer 100 may be represented by the following Equation 17 according to an embodiment.

$$z[n] = \sum_{p=0}^{P-1} \left[ \sum_{m=0}^{M-1} (w_m[n] x_{m,p}[n - \Delta_m[n] - \tau_p[n]]) \right] \quad \text{Equation 17}$$

Here, $x_{m,p}$ is a signal input through an $m^{th}$ channel in a $p^{th}$ order. That is, $x_{m,p}$ is a converted ultrasonic signal generated by an $m^{th}$ ultrasonic element $P_m$ in the $p^{th}$ order ultrasonic-wave emission. n is a distance identification value. In Equation 17, the number of channels is M, and the number of ultrasonic-wave emission times is P.

$\Delta_m[n]$ is a first time-compensation value to be processed by the time-difference compensator 110, and $T_p[n]$ is a second time-compensation value to be processed by the second time-difference compensator 120. The second time-compensation value is a value to compensate for time required for a sound field generated by an $p^{th}$ ultrasonic wave to reach a desired focal point.

$\omega_m$ is a weight to be applied to $x_{m,p}$. Here, $\omega_m$ may be a prescribed window function or apodization function. The window function may be, for example, a Hann, Hamming, rectangular window function, etc. In addition, z[n] is a resultant signal, i.e. a beamformed ultrasonic signal z.

The beamforming process performed by the beamformer 100 may be represented by the following Equation 18 according to another embodiment.

$$z[n] = \sum_{m=0}^{M-1} \left[ w_m[n] \left( \sum_{p=0}^{P-1} x_{m,p}[n - \Delta_m[n] - \tau_p[n]] \right) \right] \quad \text{Equation 18}$$

Here, $x_{m,p}$, n, $\Delta_m[n]$, $T_p[n]$, and $\omega_m$ are equal to those of Equation 17. In Equation 17, after multiplying the ultrasonic signal $x_{m,p}$ of the $m^{th}$ channel, a time difference of which has been compensated for, by the weight $\omega_m$, the multiplied signal is added by times equal in number to the number of ultrasonic-wave emission times to calculate the resultant signal z[n]. On the other hand, in Equation 18, after adding the ultrasonic signal $x_{m,p}$ of each channel, a time difference of which has been compensated for, the sum of the m channels is multiplied by the weight $\omega_m$, to calculate the resultant signal z[n], differently from Equation 17.

Here, $y_1[n]$ is defined by the following Equation 19.

$$y_{1m}[n] = \sum_{p=0}^{P-1} x_{m,p}[n - \Delta_m[n] - \tau_p[n]] \quad \text{Equation 19}$$

Using Equation 19, Equation 18 may be rearranged into the following Equation 20.

$$z[n] = \sum_{m=0}^{M-1} w_m[n] y_{1m}[n] \quad \text{Equation 20}$$

Equation 20 has the same form as that of Equation 16. Accordingly, upon calculation, $y_{1m}[n]$ may be considered as $y_m[n]$ of Equation 16. In this case, an appropriate $\omega_m[n]$ may be calculated using minimum distribution, which results in relative reduction in computational load.

Referring again to FIG. 18, the main body M may further include the image processor 300.

The image processor 300, as exemplarily shown in FIG. 18, receives the beamformed ultrasonic signal z output as the beamformer 100 implements focusing of the ultrasonic signals x. According to an embodiment, the image processor 300 of the ultrasound imaging apparatus may form an ultrasound image based on the beamformed ultrasonic signal z to allow a user, e.g., a doctor or a patient to view a subject, e.g., the interior of a human body. In addition, the image processor 300 may generate an ultrasound image substantially the same or similar to an original image based on the beamformed ultrasonic signal z using a prescribed point spread function (PSF). The image processor 300 may include a processor, a microprocessor, a central processing unit (CPU), or an integrated circuit for executing programmable instructions.

The image processor 300 may further implement post-processing on the generated ultrasound image. For instance, the image processor 300 may compensate for contrast, brightness, or sharpness of an ultrasound image. In this case, the image processor 300 may compensate for the generated ultrasound image to accentuate or attenuate only a part of the image. In the case of generating plural ultrasound images, the image processor 300 may generate a three dimensional (3D) ultrasound image using the plural ultrasound images. Additional image processing by the image processor 300 may be implemented according to predetermined settings, or may be implemented in response to a user instruction or command input via the input unit i.

The ultrasound image, reconstructed or subjected to additional image processing by the image processor 300, is transmitted to the storage unit 310 or the display unit d.

The storage unit 310 may temporarily or permanently store the ultrasound image generated or post-processed by the image processor 300.

The display unit d displays the ultrasound image, generated by the image processor 300 or stored in the storage unit 310, to the user in response to a user request or system settings, thereby allowing the user to view the internal structure or tissues of the subject ob. The display unit d may display ultrasound images to the user in real time. The display unit d may be directly installed to the main body M as exemplarily shown in FIG. 17 or FIG. 18 according to an embodiment, or may be installed to a separate workstation connected to the main body M through a wired or wireless communication network according to another embodiment.

The main body M of the ultrasound imaging apparatus may include the ultrasonic-wave generation controller 210. The ultrasonic-wave generation controller 210, according to an embodiment, may generate pulse signals in response to an instruction of the system controller 200 to transmit the pulse signals to respective ultrasonic elements P1 to P5, thereby allowing the respective ultrasonic elements P1 to P5 to generate ultrasonic waves in response to the pulse signals. In this case, the ultrasonic-wave generation controller 210 may control the plural ultrasonic elements P1 to P5 such that only some ultrasonic elements, e.g., a single ultrasonic element generates ultrasonic waves. Moreover, the ultrasonic-wave generation controller 210 may control the respective ultrasonic elements P1 to P5 or respective ultrasonic element groups to allow the respective ultrasonic elements P1 to P5 or the respective ultrasonic element groups to operate in a prescribed sequence.

The ultrasonic-wave generation controller 210, according to another embodiment, may generate a control signal for the power source 211 in response to a control instruction of the system controller 200. The power source 211 applies a prescribed alternating current to the respective ultrasonic elements P1 to P5 under control of the ultrasonic-wave generation controller 210 to vibrate a piezoelectric materials or thin film of the respective ultrasonic elements P1 to P5, thereby allowing the respective ultrasonic elements P1 to P5 to generate ultrasonic waves.

The main body M of the ultrasound imaging apparatus, as exemplarily shown in FIG. 18, may include the system controller 200. The system controller 200 controls general operations of the ultrasound imaging apparatus including the ultrasonic probe p, the beamformer 100, the ultrasonic-wave generation controller 210, the image processor 300, the storage unit 310, and the display unit d as described above. The system controller 100 may include a processor, a microprocessor, a central processing unit (CPU), or an integrated circuit for executing programmable instructions. The storage unit 310 may include a memory.

According to an embodiment, the system controller 200 may control operations of the ultrasound imaging apparatus according to predetermined system settings, or may control operations of the ultrasound imaging apparatus based on a prescribed control instruction generated in response to a user instruction or command input via the input unit i.

The input unit i receives a prescribed instruction or command from the user for control of the ultrasound imaging apparatus. The input unit I may include, for example, various user interfaces, such as a keyboard, a mouse, a trackball, or a touchscreen. According to an embodiment, the input unit i may be directly installed to the main body M, and may be provided at a workstation connected to the main body M through a wired or wireless communication network.

Figure 24:
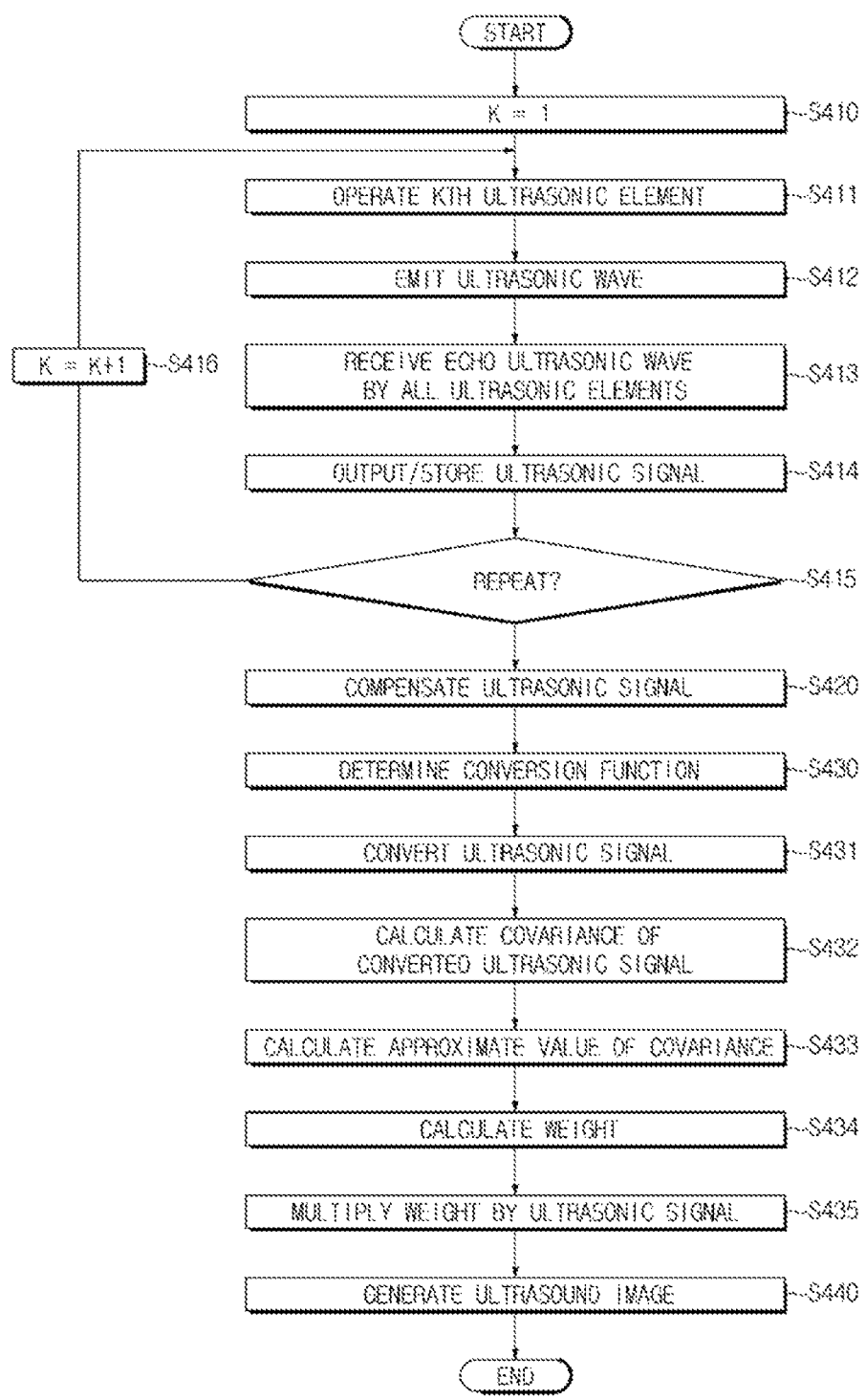
FIG. 24 is a flowchart of a control method of an ultrasound imaging apparatus according to an embodiment.

FIG. 24 is a flowchart showing a control method of an ultrasound imaging apparatus according to an embodiment.

Referring to FIG. 24, a first ultrasonic element of the ultrasonic probe P is operated (S410, S411). Ultrasonic waves are emitted to a target region and reflected from the target region (S412). All ultrasonic elements P1 to P5 receive reflected echo ultrasonic waves (S413). All of the ultrasonic elements P1 to P5 output ultrasonic signals corresponding to the received echo ultrasonic waves. The output ultrasonic signals may be stored (S414).

Next, a following ultrasonic element, e.g., a second ultrasonic element is operated (S415, S416, and S411). Likewise, ultrasonic waves are emitted to the target region (S412). In this case, a focal point of second ultrasonic-wave emission may be equal to or different from a focal point of first ultrasonic-wave emission. After all of the ultrasonic elements P1 to P5 receive echo ultrasonic waves generated upon the second ultrasonic-wave emission, ultrasonic signals corresponding to the received echo ultrasonic waves are output and stored (S411 to S415). This procedure is repeated with respect to predetermined ultrasonic elements. In this way, plural ultrasonic signals of plural channels are acquired.

Next, a time difference between the plural ultrasonic signals of the plural channels is compensated for (S420). More specifically, a time difference depending on time required for the emitted ultrasonic waves to reach a desired target region and a time difference depending on time required for ultrasonic waves reflected from the target region to reach the respective ultrasonic elements may be compensated for.

Next, a conversion function is determined (S430). In this case, the conversion function may be predefined, or may be selected from among plural prestored conversion functions. In addition, a conversion function may be generated using at least one basis vector. The conversion function may vary according to the plural ultrasonic signals of the plural channels.

Next, the ultrasonic signal, using the conversion function, are converted (S431), and covariance with respect to the converted ultrasonic signal is calculated (S432). According to an embodiment, covariance with respect to the ultrasonic signals may be calculated without conversion of the ultrasonic signals.

An approximate value of the calculated covariance is calculated (S433). According to an embodiment, the approximate value of the calculated covariance may be expressed in the form of an approximate matrix, e.g., in the form of a Toeplitz matrix.

Next, a prescribed weight is calculated using the approximate value of the covariance (S434). In this case, the calculated weight may be a beamforming coefficient for use in beamforming. The prescribed weight, for instance, may be a converted ultrasonic signal weight β, or an ultrasonic signal weight ω. According to an embodiment, the prescribed weight may be calculated by calculating an inverse-matrix of the approximate value of the covariance, e.g., the approximate value in the form of a Toeplitz matrix, and substituting the calculated inverse-matrix into Equation 9. In this case, the calculated weight may be the converted ultrasonic signal weight β for use in synthesis of the converted signals. After calculation of the converted ultrasonic signal weight β, the calculated converted-signal weight β is converted using a conversion function to calculate the ultrasonic signal weight ω for use in beamforming of ultrasonic signals.

The ultrasonic signals or converted ultrasonic signals are synthesized using the calculated prescribed weight to implement beamforming (S435). In the case of synthesizing ultrasonic signals, the prescribed weight may be the ultrasonic signal weight ω. In the case of synthesizing converted ultrasonic signals, the prescribed weight may be the converted ultrasonic signal weight β.

More specifically, in the case of synthesizing ultrasonic signals or converted ultrasonic signals, according to an embodiment, plural ultrasonic signals or plural converted ultrasonic signals input to each channel are first synthesized to acquire synthesized ultrasonic signals of plural channels or synthesized converted ultrasonic signals of plural channels. Next, the synthesized ultrasonic signals of plural channels or the synthesized converted ultrasonic signals of plural channels may again be synthesized using the ultrasonic signal weight ω or the converted ultrasonic signal weight β.

According to another embodiment, ultrasonic signals of plural channels or converted ultrasonic signals of plural channels may be first synthesized using the ultrasonic signal weight ω or the converted ultrasonic signal weight β, and the plural synthesized ultrasonic signals or the plural synthesized converted ultrasonic signals may again be synthesized.

As a result, the beamformed ultrasonic signal z may be acquired.

Next, a final ultrasound image is generated using the beamformed ultrasonic signal z (S440). According to an embodiment, after a point spread function may be applied to the beamformed ultrasonic signal z for further compensation, a final ultrasound image is generated. Post processing may further be performed on the generated ultrasound image.

As is apparent from the above description, according to an image processing module, an ultrasound imaging apparatus, an image processing method, and a control method of an ultrasound imaging apparatus as described above, performance of various devices using beamforming may be enhanced, and high-quality images may be acquired without requiring increased computational load during image processing.

Also, improved-quality beamforming results may be acquired without increasing computational load during beamforming or while reducing the computational load, and thus image quality or resolution as well as signal to noise ratio may be enhanced.

Further, resources required for beamforming by various devices that implement beamforming according to the exemplary embodiments may be reduced, and overload of the devices may be prevented. Furthermore, reduction in resource usage of the beamforming devices may advantageously reduce power consumption of the various devices or simplify the specifications of a calculator, which may result in reduced cost.

In addition, an enhanced beamforming calculation speed may be accomplished via an increased beamforming speed and reduced beamforming time with respect to input signals, which enables rapid processing of beamforming of devices that require beamforming.

In a variety of imaging apparatuses using an image processing module, e.g., ultrasound imaging apparatuses, ultrasound images may be calculated and generated to be displayed to the user in real time.

Although a few exemplary embodiments have been shown and described, it would be appreciated by those skilled in the art that many alternatives, modifications, and variations may be made in these embodiments without departing from the principles and spirit of the disclosure, the scope of which is defined in the claims and their equivalents.

What is claimed is:

1. An image processing module comprising:
an input unit configured to receive a plurality of input signals from each of a plurality of channels;
a conversion function database including at least one conversion function;
a processor configured to synthesize a plurality of input signals that are sequentially received from a same channel among the plurality of channels to acquire at least one synthesized input signal, and convert the synthesized input signal to acquire at least one converted signal using a conversion function selected from the at least one conversion function in the conversion function database,
wherein the processor is further configured to:
calculate at least one weight to be applied to each channel based on the at least one converted signal; and
synthesize the plurality of input signals of the plurality of channels using the at least one weight,
wherein the processor is further configured to synthesize at least a portion of the plurality of input signals of the plurality of channels using the at least one weight to generate a plurality of synthesized input signals, and resynthesize the plurality of the synthesized input signals.

2. The image processing module according to claim 1, wherein the processor is further configured to synthesize the plurality of input signals of each channel with respect to the plurality of channels, respectively, so that a plurality of synthesized input signals of the plurality of channels are generated, and to resynthesize the plurality of synthesized input signals of the plurality of channels using the at least one weight.

3. The image processing module according to claim 1, wherein the at least one weight comprises at least one of an input signal weight to be applied to at least one input signal of each channel and a converted signal weight to be applied to the at least one converted signal.

4. The image processing module according to claim 3, wherein the input signal weight is acquired by converting the converted signal weight.

5. The image processing module according to claim 1, wherein the processor is further configured to calculate covariance with respect to a plurality of converted signals, and calculates the at least one weight based on an approximate value of the calculated covariance.

6. The image processing module according to claim 5, wherein the processor is further configured to calculate a Toeplitz matrix approximate to the calculated covariance, and calculates the at least one weight using the Toeplitz matrix.

7. The image processing module according to claim 6, wherein the processor is further configured to calculate an inverse-matrix of the Toeplitz matrix, and calculates a converted signal weight to be applied to the at least one converted signal based on the calculated inverse-matrix.

8. The image processing module according to claim 7, wherein the processor is further configured to calculate at least one input signal weight to be applied to at least one input signal of each channel by converting the converted signal weight.

9. The image processing module according to claim 7, wherein the processor is further configured to multiply the converted signal weight by the at least one converted signal to synthesize the plurality of input signals of the plurality of channels.

10. An image processing method comprising:
receiving a plurality of input signals from each of a plurality of channels;
acquiring a conversion function from a conversion function database;
acquiring at least one converted signal by synthesizing a plurality of input signals that are sequentially received from a same channel among the plurality of channels to acquire at least one synthesized input signal, and converting the synthesized input signal into at least one converted signal using the acquired conversion function;
calculating at least one weight to be applied to each channel based on the at least one converted signal; and
synthesizing the plurality of input signals using the at least one weight,
wherein the synthesizing comprises synthesizing the input signals of the plurality of channels using the at least one weight to generate a plurality of synthesized input signals, and resynthesizing the synthesized input signals.

11. The image processing method according to claim 10, wherein the synthesizing comprises synthesizing a plurality of synthesized input signals of the plurality of channels, and resynthesizing the plurality of synthesized input signals of the plurality of channels using the at least one weight.

12. The image processing method according to claim 10, wherein the calculating comprises:
calculating covariance with respect to the at least one converted signal;
calculating an approximate value of the calculated covariance;
calculating at least one of an input signal weight to be applied to the at least one input signal and a converted signal weight to be applied to the at least one converted signal based on the calculated approximate value; and
generating a synthesized signal using the at least one of the input signal weight and the converted signal weight.

* * * * *